US012781235B2

(12) United States Patent
Hu et al.

(10) Patent No.: US 12,781,235 B2
(45) Date of Patent: Nov. 3, 2026

(54) **METHOD FOR SYNTHESIS, ASSEMBLY AND FUNCTION TEST OF ARTIFICIAL CHLOROPLAST GENOME OF *Chlamydomonas reinhardtii***

(71) Applicant: SHENZHEN UNIVERSITY, Shenzhen (CN)

(72) Inventors: Zhangli Hu, Shenzhen (CN); Chaogang Wang, Shenzhen (CN); Chunli Guo, Shenzhen (CN); Guiying Zhang, Shenzhen (CN); Bin Jia, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 454 days.

(21) Appl. No.: 18/559,847

(22) PCT Filed: Aug. 12, 2022

(86) PCT No.: PCT/CN2022/112271
§ 371 (c)(1),
(2) Date: Nov. 9, 2023

(87) PCT Pub. No.: WO2024/026923
PCT Pub. Date: Feb. 8, 2024

(65) Prior Publication Data

US 2025/0092407 A1 Mar. 20, 2025

(30) Foreign Application Priority Data

Aug. 1, 2022 (CN) ......................... 202210917993.3

(51) Int. Cl.
*C12N 15/81* (2006.01)
*C12N 15/82* (2006.01)
(Continued)

(52) U.S. Cl.
CPC ......... *C12N 15/81* (2013.01); *C12N 15/8207* (2013.01); *C12N 15/905* (2013.01);
(Continued)

(58) Field of Classification Search
CPC .. C12N 15/81; C12N 15/8207; C12N 15/905; C12N 3/00; C12N 15/00; C12N 15/09;
(Continued)

(56) References Cited

U.S. PATENT DOCUMENTS

| | | | | |
|---|---|---|---|---|
| 7,129,391 | B1 | 10/2006 | Daniell | |
| 2007/0264688 | A1* | 11/2007 | Venter ................ | C12N 15/1093 435/325 |
| 2015/0329898 | A1 | 11/2015 | Bogden et al. | |

FOREIGN PATENT DOCUMENTS

| | | | |
|---|---|---|---|
| CN | 1807649 | A | 7/2006 |
| CN | 1827769 | A | 9/2006 |

(Continued)

OTHER PUBLICATIONS

Sizova, I., Fuhrmann, M., & Hegemann, P. (2001). A *Streptomyces rimosus* aphVIII gene coding for a new type phosphotransferase provides stable antibiotic resistance to *Chlamydomonas reinhardtii*. Gene, 277(1-2), 221-229. (Year: 2001).*

(Continued)

*Primary Examiner* — Anne M. Gussow
*Assistant Examiner* — Amelia Stephens
(74) *Attorney, Agent, or Firm* — Maier & Maier, PLLC

(57) ABSTRACT

A method for synthesis, assembly and function test of an artificial chloroplast genome of *Chlamydomonas reinhardtii*. Rational design has been carried out on the *Chlamydomonas reinhardtii* chloroplast genome for the first time, and total artificial synthesis of the *Chlamydomonas reinhardtii* chloroplast genome is proposed. By using totally chemically synthesized chloroplast genome segments, total chemical de (Continued)

novo synthesis and assembly of a chloroplast genome are achieved in a yeast-bacterium system. Then, a totally chemically synthesized chloroplast genome is transformed into *Chlamydomonas* cells to replace the original chloroplast genome, which works normally, and has been verified, fulfilling biological functions of the totally chemically synthesized chloroplast genome. According to the embodiments, the *Chlamydomonas reinhardtii* chloroplast genome is an efficient platform for carrying out synthetic biology operation.

4 Claims, 8 Drawing Sheets

Specification includes a Sequence Listing.

(51) Int. Cl.
*C12N 15/90* (2006.01)
*C12Q 1/6895* (2018.01)
*G01N 33/569* (2006.01)

(52) U.S. Cl.
CPC ..... *C12Q 1/6895* (2013.01); *G01N 33/56961* (2013.01); *C12Q 2600/156* (2013.01); *G01N 2333/405* (2013.01); *G01N 2474/10* (2021.08)

(58) Field of Classification Search
CPC ........ C12N 15/11; C12N 15/66; C12N 15/74; C12N 15/79; C12N 15/82; C12N 15/8214; C12N 15/90; C12Q 1/6895; C12Q 2600/156; C12Q 1/04; G01N 33/56961; G01N 2333/405; G01N 2474/10; C07K 14/415; C07K 14/00; C12R 2001/85; C12P 21/00; Y02E 50/10
See application file for complete search history.

(56) References Cited

FOREIGN PATENT DOCUMENTS

| | | | | | |
|---|---|---|---|---|---|
| CN | 101939423 | A | | 1/2011 | |
| CN | 102146344 | A | | 8/2011 | |
| CN | 102630140 | A | | 8/2012 | |
| CN | 104480130 | A | | 4/2015 | |
| CN | 105821072 | A | | 8/2016 | |
| CN | 106754393 | A | | 5/2017 | |
| CN | 106967749 | A | | 7/2017 | |
| CN | 107267538 | A | | 10/2017 | |
| CN | 111088289 | A | | 5/2020 | |
| GB | 2475435 | A | | 5/2011 | |
| WO | WO-2009045550 | A2 | * | 4/2009 | ............. C12N 15/82 |

OTHER PUBLICATIONS

Croning, M.D., Fricker, D.G., Komiyama, N.H et al. Automated design of genomic Southern blot probes. BMC Genomics 11, 74 (2010) (Year: 2010).*
Meslet-Cladiere, L., & Vallon, O. (2011). Novel shuttle markers for nuclear transformation of the green alga *Chlamydomonas reinhardtii*. Eukaryotic cell, 10(12), 1670-1678. (Year: 2011).*
O'Neill, B. M., Mikkelson, K. L., Gutierrez, N. M., Cunningham, J. L., Wolff, K. L., Szyjka, S. J., . . . & Mendez, M. J. (2012). An exogenous chloroplast genome for complex sequence manipulation in algae. Nucleic Acids Research, 40(6), 2782-2792. (Year: 2012).*
Zhao, X., Li, G., & Liang, S. (2013). Several affinity tags commonly used in chromatographic purification. Journal of analytical methods in chemistry, 2013(1), 581093. (Year: 2013).*
Wannathong, T., Waterhouse, J. C., Young, R. E., Economou, C. K., & Purton, S. (2016). New tools for chloroplast genetic engineering allow the synthesis of human growth hormone in the green alga *Chlamydomonas reinhardtii*. Applied microbiology and biotechnology, 100(12), 5467-5477. (Year: 2016).*
Larrea-Alvarez, M., & Purton, S. (2020). Multigenic engineering of the chloroplast genome in the green alga *Chlamydomonas reinhardtii*. Microbiology, 166(6), 510-515. (Year: 2020).*
Katherine, A. (2017). Guidelines for formatting gene and protein names. (Year: 2017).*
Chinese Office Action issued on Jun. 6, 2023, in corresponding application No. 202210917993.3; 11 pages.
Wei Jianhe et al., "Biotechnology of Traditional Chinese Medicine, 9th ed." China Traditional Chinese Medicine Publishing, Feb. 28, 2017, 4 pages.
Laurence Meslet-Cladiere et al., "Novel Shuttle Markers for Nuclear Transformation of the Green Alga *Chlamydomonas reinhardtii*", Eukaryotic Cell, vol. 10, No. 12, Dec. 2011, p. 1670-1678, 9 pages.
Maul, J.E et al., "*Chlamydomonas reinhardtii* chloroplast, complete genome", NCBI-BLAST, Jan. 23, 2004, 1 page.
Chinese Office Action issued on Aug. 10, 2023, in corresponding application No. 202210917993.3; 7 pages.
Chinese Office Action issued on Nov. 6, 2023, in corresponding application No. 202210917993.3; 9 pages.
International Search Report issued on Mar. 24, 2023 in corresponding application No. PCT/CN2022/112271; 11 pages.
Han Sihai et al., "Exppession of Foreign Genes in *Chlamydomonas reinhardtii* Chloroplast", Biotechnology Bulletin, 1st Issue, Jan. 31, 2007, (Jan. 31, 2007), pp. 89-94, 6 pages.
Wang Chao-gang et al., "The research advance in nuclear transformation system of *Chlamydomonas reinhardtii*" Journal of Zhongkai University of Agriculture and Technology, vol. 18, No. 2, Dec. 31, 2005 (Dec. 31, 2005), pp. 59-64, 6 pages.
Kuck, U. et al., "The Chloroplast Trans-Splicing RNA-Protein Supercomplex from the Green Alga *Chlamydomonas reinhardtii*", vol. 10, Feb. 1, 2021 (Feb. 1, 2021), title 290, pp. 1-23, 23 pages.
Kathir, P. et al., "Molecular Map of the *Chlamydomonas reinhardtii* Nuclear Genome", Eukaryotic Cell, vol. 2, No. 2, Apr. 30, 2003 (Apr. 30, 2003), pp. 362-379, 18 pages.

* cited by examiner

Intermediate plasmid 1
92,477 bp

CC5168 (dark) CC5168-1 CC5168-2 CC5168-3

SEQUENCE LISTING

```
Sequence total quantity: 16
SEQ ID NO: 1            moltype = DNA  length = 27
FEATURE                 Location/Qualifiers
source                  1..27
                        mol_type = other DNA
                        organism = synthetic construct
SEQUENCE: 1
agcttcatag tttgaaaaac gtgcacc                                        27

SEQ ID NO: 2            moltype = DNA  length = 27
FEATURE                 Location/Qualifiers
source                  1..27
                        mol_type = other DNA
                        organism = synthetic construct
SEQUENCE: 2
gctttgcaaa aggcagacaa atttacc                                        27

SEQ ID NO: 3            moltype = DNA  length = 21
FEATURE                 Location/Qualifiers
source                  1..21
                        mol_type = other DNA
                        organism = synthetic construct
SEQUENCE: 3
aagaagctgt aaccgtaccc c                                              21

SEQ ID NO: 4            moltype = DNA  length = 21
FEATURE                 Location/Qualifiers
source                  1..21
                        mol_type = other DNA
                        organism = synthetic construct
SEQUENCE: 4
agaccgtgta attcgtcacc g                                              21

SEQ ID NO: 5            moltype = DNA  length = 11060
FEATURE                 Location/Qualifiers
source                  1..11060
                        mol_type = other DNA
                        organism = synthetic construct
SEQUENCE: 5
gctcacgtga cgcgtctcga gaagctttcc tgtgtgaaat tgttatccgc tcgccggcgg  60
ctgctaacaa agcccgaaag gaagctgagt tggctgctgc caccgctgag caataactag  120
cataacccct tggggcctct aaacgggtct tgaggggttt tttgctgaaa ggaggaacta  180
tatccggatg accgacctgt ccggtgccct gaatgaactg caggacgagt aatcacactg  240
gctcaccttc gggtgggcct ttctgcgttt atgctagtga taataagtga ctgaggtatg  300
tgctcttctt atctcctttt gtagtgttgc tcttatttta aacaactttg cggtttttg  360
atgactttgc gattttgttg ttgctttgca gtaaattgca agatttaata aaaaaacgca  420
aagcaatgat taaaggatgt tcagaatgaa actcatggaa acacttaacc agtgcataaa  480
cgctggtcat gaaatgacga aggctatcgc cattgcacag tttaatgatg acagcccgga  540
agcgaggaaa ataacccggc gctggagaat aggtgaagca gcggatttag ttggggtttc  600
ttctcaggct atcagagatg ccgagaaagc agggcgacta ccgcacccgg atatggaaat  660
tcgaggacgg gttgagcaac gtgttggtta tacaattgaa caaattaatc atatgcgtga  720
tgtgtttggt acgcgattgc gacgtgctga agacgtattt ccaccggtga tcggggttgc  780
tgcccataaa ggtggcgttt acaaaacctc agtttctgtt catcttgctc aggatctggc  840
tctgaagggg ctacgtgttt tgctcgtgga aggtaacgac ccccagggaa cagcctcaat  900
gtatcacgga tgggtaccag atctcatgat tcatgcagaa gacactctcc tgcctttcta  960
tcttggggaa aaggacgatg tcacttatgc aataaagccc acttgctggc cggggcttga  1020
cattattcct tcctgtctgg ctctgcaccg tattgaaact gagttaatgg gcaaatttga  1080
tgaaggtaaa ctgcccaccg atccacacct gatgctccga ctggccattg aaactgttgc  1140
tcatgactat gatgtcatag ttattgacag cgcgcctaac ctgggtatcg gcacgattaa  1200
tgtcgtatgt gctgctgatg tgctgattgt tcccacgcct gctgagttgt ttgactacac  1260
ctccgcactg cagtttttcg atatgcttcg tgatctgctc aagaacgttg atcttaaagg  1320
gttcgagcct gatgtacgta ttttgcttac caaatacagc aatagtaatg gctctcagtc  1380
cccgtggatg gaggagcaaa ttcgggatgc ctggggaagc atggttctaa aaaatgttgt  1440
acgtgaaacg gatgaagttg gtaaaggtca gatccggatg agaactgttt ttgaacaggc  1500
cattgatcaa cgctcttcaa ctggtgcctg gagaaatgct ctttctattt gggaacctgt  1560
```

-continued

```
ctgcaatgaa attttcgatc gtctgattaa accacgctgg gagattagat aatgaagcgt  1620
gcgcctgtta ttccaaaaca tacgctcaat actcaaccgg ttgaagatac ttcgttatcg  1680
acaccagctg ccccgatggt ggattcgtta attgcgcgcg taggagtaat ggctcgcggt  1740
aatgccatta ctttgcctgt atgtggtcgg gatgtgaagt ttactcttga agtgctccgg  1800
ggtgatagtg ttgagaagac ctctcgggta tggtcaggta atgaacgtga ccaggagctg  1860
cttactgagg acgcactgga tgatctcatc ccttcttttc tactgactgg tcaacagaca  1920
ccggcgttcg gtcgaagagt atctggtgtc atagaaattg ccgatgggag tcgccgtcgt  1980
aaagctgctg cacttaccga aagtgattat cgtgttctgg ttggcgagct ggatgatgag  2040
cagatggctg cattatccag attgggtaac gattatcgcc caacaagtgc ttatgaacgt  2100
ggtcagcgtt atgcaagccg attgcagaat gaatttgctg gaaatatttc tgcgctggct  2160
gatgcggaaa atatttcacg taagattatt acccgctgta tcaacaccgc caaattgcct  2220
aaatcagttg ttgctctttt ttctcacccc ggtgaactat ctgcccggtc aggtgatgca  2280
cttcaaaaag cctttacaga taaagaggaa ttacttaagc agcaggcatc taaccttcat  2340
gagcagaaaa aagctggggt gatatttgaa gctgaagaag ttatcactct tttaacttct  2400
gtgcttaaaa cgtcatctgc atcaagaact agtttaagct cacgacatca gtttgctcct  2460
ggagcgacag tattgtataa gggcgataaa atggtgctta acctggacag gtctcgtgtt  2520
ccaactgagt gtatagagaa aattgaggcc attcttaagg aacttgaaaa gccagcaccc  2580
tgatgcgacc acgttttagt ctacgtttat ctgtctttac ttaatgtcct ttgttacagg  2640
ccagaaagca taactggcct gaatattctc tctgggccca ctgttccact tgtatcgtcg  2700
gtctgataat cagactggga ccacggtccc actcgtatcg tcggtctgat tattagtctg  2760
ggaccacggt cccactcgta tcgtcggtct gattattagt ctgggaccac ggtcccactc  2820
gtatcgtcgg tctgataatc agactgggac cacggtccca ctcgtatcgt cggtctgatt  2880
attagtctgg gaccatggtc ccactcgtat cgtcggtctg attattagtc tgggaccacg  2940
gtcccactcg tatcgtcggt ctgattatta gtctggaacc acggtcccac tcgtatcgtc  3000
ggtctgatta ttagtctggg accacggtcc cactcgtatc gtcggtctga ttattagtct  3060
gggaccacga tcccactcgt gttgtcggtc tgattatcgg tctgggacca cggtcccact  3120
tgtattgtcg atcagactat cagcgtgaga ctacgattcc atcaatgcct gtcaagggca  3180
agtattgaca tgtcgtcgta acctgtagaa cggagtaacc tcggtgtgcg gttgtatgcc  3240
tgctgtggat tgctgctgtg tcctgcttat ccacaacatt ttgcgcacgg ttatgtggac  3300
aaaatacctg gttacccagg ccgtgccggc acgttaaccg ggctgcatcc gatgcaagtg  3360
tgtcgctgtc gacgagctcg cgagctcgga catgaggttg ccccgtattc agtgtcgctg  3420
atttgtattg tctgaagttg tttttacgtt aagttgatgc agatcaatta atacgatacc  3480
tgcgtcataa ttgattattt gacgtggttt gatggcctcc acgcacgttg tgatatgtag  3540
atgataatca ttatcacttt acgggtcctt tccggtgatc cgacaggtta cggggcggcg  3600
acctcgcggg ttttcgctat ttatgaaaat tttccggttt aaggcgtttc cgttcttctt  3660
cgtcataact taatgttttt atttaaaata ccctctgaaa agaaaggaaa cgacaggtgc  3720
tgaaagcgag ctttttggcc tctgtcgttt cctttctctg tttttgtccg tggaatgaac  3780
aatggaagtc cgagctcatc gctaataact tcgtatagca tacattatac gaagttatat  3840
tcgatgctgc ctggcggcag tagcgcggtg gtcccacctg accccatgcc gaactcagaa  3900
gtgaaacgcc gtagcgccga tggtagtgtg gggtctcccc atgcgagagt agggaactgc  3960
caggcatcaa ataaaacgaa aggctcagtc gaaagactgg gccttcctgc cactcatcgc  4020
agtactgttg taattcatta agcatgcaga aagtcaaaag cctccgaccg gaggcttttg  4080
actattactg ccgacatgga agccatcaca aacggcatga tgaacctata aacgcagaaa  4140
ggcccacccg aaggtgagcc agtgtgatta ccagcggcat cagcaccttg tcgccttgcg  4200
tataatattt gcaaaaaacc cctcaagacc cgtttagagg ccccaagggg ttatgctagg  4260
cccgggcgtc tgacgctcag tggaacgaaa actcacgtta agggattttg gtcatgagat  4320
tatcaaaaag gatcttcacc tagatccttt taaattaaaa atgaagtttt aaatcaatct  4380
aaagtatata tgagtaaact tggtctgaca gttaccaatg cttaatcagt gaggcaccta  4440
tctcagcgat ctgtctattt cgttcatcca tagttgcctg actccccgtc gtgtagataa  4500
ctacgatacg ggagggctta ccatctggcc ccagtgctgc aatgataccg cgactaccac  4560
gctcaccggc tccagattta tcagcaataa accagccagc cggaagggcc gagcgcagaa  4620
gtggtcctgc aactttatcc gcctccatcc agtctattaa ttgttgccgg gaagctagag  4680
taagtagttc gccagttaat agtttgcgca acgttgttgc cattgctaca ggcatcgtgg  4740
tgtcacgctc gtcgtttggt atggcttcat tcagctccgg ttcccaacga tcaaggcgag  4800
ttacatgatc ccccatgttg tgcaaaaaag cggttagctc cttcggtcct ccgatcgttg  4860
tcagaagtaa gttggccgca gtgttatcac tcatggttat ggcagcactg cataattctc  4920
ttactgtcat gccatccgta agatgctttt ctgtgactgg tgagtactca accaagtcat  4980
tctgagaata gtgtatgcgg cgaccgagtt gctcttgccc ggcgtcaata cgggataata  5040
ccgcgccaca tagcagaact ttaaaagtgc tcatcattgg aaaacgttct tcggggcgaa  5100
aactctcaag gatcttaccg ctgttgagat ccagttcgat gtaacccact cgtgcaccca  5160
actgatcttc agcatctttt actttcacca gcgtttctgg gtgagcaaaa acaggaaggc  5220
aaaatgccgc aaaaaaggga ataagggcga cacggaaatg ttgaatactc atactcttcc  5280
tttttcaata ttattgaagc atttatcagg gttattgtct catgagcgga tacatatttg  5340
aatgtattta gaaaaataaa caaatagggg ttccgcgcac atttccccga aaagtgccac  5400
ctgggtcctt ttcatcacgt gctataaaaa taattataat ttaaattttt taatataaat  5460
atataaatta aaaatagaaa gtaaaaaaag aaattaaaga aaaaatagtt tttgttttcc  5520
gaagatgtaa aagactctag gggatcgcc aacaaatact accttttatc ttgctcttcc  5580
tgctctcagg tattaatgcc gaattgtttc atcttgtctg tgtagaagac cacacacgaa  5640
aatcctgtga ttttacattt tacttatcgt taatcgaatg tatatctatt taatctgctt  5700
ttcttgtcta ataaatatat atgtaaagta cgctttttgt tgaaattttt taaacctttg  5760
tttatttttt tttcttcatt ccgtaactct tctaccttct ttatttactt tctaaaatcc  5820
aaatacaaaa cataaaaata aataaacaca gagtaaattc ccaaattatt ccatcattaa  5880
aagatacgag gcgcgtgtaa gttacaggca agcgatccgt ctaagaaacc attattatca  5940
tgacattaac ctataaaaat aggcgtatca cgaggccctt taatctcgcg cgtttcggtg  6000
atgacggtga aaacctctga cacatgcagc tcccggagat tgtcacagct tgtctgtaag  6060
cggatgccgg gagcagacaa gcccgtcagg gcgcgtcagc gggtgttggc gggtgtcggg  6120
gctggcttaa ctatgcggca tcagagcaga ttgtactgag agtgcaccat atcgactacg  6180
tcgttaaggc cgtttctgac agagtaaaat tcttgaggga actttcacca ttatgggaaa  6240
tggttcaaga aggtattgac ttaaactcca tcaaatggtc aggtcattga gtgtttttta  6300
```

-continued

```
tttgttgtat tttttttttt ttagagaaaa tcctccaata tataaattag gaatcatagt  6360
ttcatgattt tctgttacac ctaacttttt gtgtggtgcc ctcctccttg tcaatattaa  6420
tgttaaagtg caattctttt tccttatcac gttgagccat tagtatcaat ttgcttacct  6480
gtattccttt acatcctcct ttttctcctt cttgataaat gtatgtagat tgcgtatata  6540
gtttcgtcta ccctatgaac atattccatt ttgtaatttc gtgtcgtttc tattatgaat  6600
ttcatttata aagtttatgt acaaatatca taaaaaaaga gaatcttttt aagcaaggat  6660
tttcttaact tcttcggcga cagcatcatt agttttgctg gccgcatctt ctcaaatatg  6720
cttcccagcc tgcttttctg taacgttcac cctctacctt agcatccctt ccctttgcaa  6780
atagtcctct tccaacaata ataatgtcag atcctgtaga gaccacatca tccacggttc  6840
tatactgttg acccaatgcg tctcccttgt catctaaacc cacaccgggt gtcataatca  6900
accaatcgta accttcatct cttccaccca tgtctctttg agcaataaag ccgataacaa  6960
aatctttgtc gctcttcgca atgtcaacag taccctttagt atattctcca gtagataggg  7020
agcccttgca tgacaattct gctaacatca aaaggcctct aggttccttt gttacttctt  7080
ctgccgcctg cttcaaaccg ctaacaatac ctgggcccac cacaccgtgt gcattcgtaa  7140
tgtctgccca ttctgctatt ctgtatacac ccgcagagta ctgcaatttg actgtattac  7200
caatgtcagc aaattttctg tcttcgaaga gtaaaaaatt gtacttggcg gataatgcct  7260
ttagcggctt aactgtgccc tccatggaaa aatcagtcaa gatatccaca tgtgttttta  7320
gtaaacaaat tttgggacct aatgcttcaa ctaactccag taattccttg gtggtacgaa  7380
catccaatga agcacacaag tttgtttgct tttcgtgcat gatattaaat agcttggcag  7440
caacaggact aggatgagta gcagcacgtt ccttatatgt agctttcgac atgatttatc  7500
ttcgtttcct gcaggttttt gttctgtgca gttgggttaa gaatactggg caatttcatg  7560
tttcttcaac actacatatg cgtatatata ccaatctaag tctgtgctcc ttccttcgtt  7620
cttccttctg ttcggagatt accgaatcaa aaaaatttca aagaaaccga aatcaaaaaa  7680
aagaataaaa aaaaaatgat gaattgaatt gaaaagctgt ggtatggtgc actctcagta  7740
caactgcggt caagatattt cttgaatcag gcgccttaga ccgctcggcc aaacaaccaa  7800
ttacttgttg agaaatagag tataattatc ctataaatat aacgtttttg aacacacatg  7860
aacaaggaag tacaggacaa ttgattttga agagaatgtg gattttgatg taattgttgg  7920
gattccattt ttaataaggc aataatatta ggtatgtgga tatactagaa gttctcctcg  7980
accgtcgata tgcggtgtga aataccgcac agatgctacc gctgaaagtt ctgcaaagcc  8040
tgatgggaca taagtccatc agttcaacgg aagtctacac gaaggttttt gcgctggatg  8100
tggctgcccg gcaccgggtg cagtttgcga tgccggagtc tgatgcggtt gcgatgctga  8160
aacaattatc ctgagaataa atgccttggc ctttatatgg aaatgtggaa ctgagtggat  8220
atgctgtttt tgtctgttaa acagagaagc tggctgttat ccactgagaa gcgaacgaaa  8280
cagtcgggaa aatctcccat tatcgtagag atccgcatta ttaatctcag gagcctgtgt  8340
agcgtttata ggaagtagtg ttctgtcatg atgcctgcaa gcggtaacga aaacgatttg  8400
aatatgcctt caggaacaat agaaatcttc gtgcggtgtt acgttgaagt ggagcggatt  8460
atgtcagcaa tggacagaac aacctaatga acacagaacc atgatgtggt ctgtcctttt  8520
acagccagta gtgctcgccg cagtcgagcg acagggcgaa gccctcggct ggttgccctc  8580
gccgctgggc tggcggccgt ctatggccct gcaaacgcgc cagaaacgcc gtcgaagccg  8640
tgtgcgagac accgcggccg gccgccggct ttgtggatac ctcgcggaaa acttggccct  8700
cactgacaga tgaggggcgg acgttgacac ttgaggggcc gactcacccg gcgcggcgtt  8760
gacagatgag ggcaggctc gatttcggcc ggcgacgtgg agctggccag cctcgcaaat  8820
cggcgaaaac gcctgatttt acgcgagttt cccacagatg atgtggacaa gcctggggat  8880
aagtgccctg cggtattgac acttgagggg cgcgactact gacagatgag ggcgcgatc  8940
cttgacactt gaggggcaga gtgctgacag atgaggggcg cacctattga catttgaggg  9000
gctgtccaca ggcagaaaat ccagcatttg caagggtttc cgcccgtttt tcggccaccg  9060
ctaacctgtc ttttaacctg cttttaaacc aatatttata aaccttgttt ttaaccaggg  9120
ctgcgccctg tgcgcgtgac cgcgcacgcc gaaggggggt gcccccctt ctcgaaccct  9180
cccggtcgag tgagcgagga agcaccaggg aacagcactt atatattctg cttacacacg  9240
atgcctgaaa aaacttccct tggggttatc cacttatcca cggggatatt tttataatta  9300
ttttttttat agtttttaga tcttcttttt tagagcgcct tgtaggcctt tatccatgct  9360
ggttctagag aaggtgttgt gacaaattgc cctttcagtg tgacaaatca ccctcaaatg  9420
acagtcctgt ctgtgacaaa ttgcccttaa ccctgtgaca aattgccctc agaagaagct  9480
gtttttcac aaagttatcc ctgcttattg actctttttt atttagtgtg acaatctaaa  9540
aacttgtcac acttcacatg gatctgtcat ggcggaaaca gcggttatca atcacaagaa  9600
acgtaaaaat agcccgcgaa tcgtccagtc aaacgacctc actgaggcgg catatagtct  9660
ctcccgggat caaaaacgta tgctgtatct gttcgttgac cagatcagaa aatctgatgg  9720
caccctacag gaacatgacg gtatctgcga gatccatgtt gctaaatatg ctgaaatatt  9780
cggattgacc tctgcggaag ccagtaagga tatacggcag gcattgaaga gtttcgcggg  9840
gaaggaagtg gtttttatc gccctgaaga ggatgccggc gatgaaaaag gctatgaatc  9900
ttttccttgg tttatcaaac gtgcgcacag tccatccaga gggctttaca gtgtacatat  9960
caacccatat ctcattccct tctttatcgg gttacagaac cggtttacgc agtttcggct  10020
tagtgaaaca aaagaaatca ccaatccgta tgccatgcgt ttatacgaat ccctgtgtca  10080
gtatcgtaag ccggatggct caggcatcgt ctctctgaaa atcgactgga tcatagagcg  10140
ttaccagctg cctcaaagtt accagcgtat gcctgacttc cgccgccgct tcctgcaggt  10200
ctgtgttaat gagatcaaca gcagaactcc aatgcgcctc tcatacattg agaaaaagaa  10260
aggccgccag acgactcata tcgtattttc cttccgcgat atcacttcca tgacgacagg  10320
atagtctgag ggttatctgt cacagatttg agggtggttc gtcacatttg ttctgaccta  10380
ctgagggtaa tttgtcacag ttttgctgtt tccttcagcc tgcatggatt ttctcatact  10440
ttttgaactg taatttttaa ggaagccaaa tttgagggca gtttgtcaca gttgatttcc  10500
ttctctttcc cttcgtcatg tgacctgata tcgggggtta gttcgtcatc attgatgagg  10560
gttgattatc acagtttatt actctgaatt ggctatccgc gtgtgtacct ctacctggag  10620
tttttcccac ggtggatatt tcttcttgcg ctgagcgtaa gagctatctg acagaacagt  10680
tcttctttgc ttcctcgcca gttcgctcgc tatgctcggt tacacggctg cggcgagctg  10740
cctggcggca gtagcgcggt ggtcccacct gaccccatgc cgaactcaga agtgaaacgc  10800
cgtagcgccg atggtagtgt ggggtctccc catgcgagag tagggaactg ccaggcatca  10860
aataaaacga aaggctcagt cgaaagactg ggccttggat tgcacgcagg ttctccggcc  10920
gcttgggtgg agaggcgcag aaagtcaaaa gcctccgacc ggaggctttt gactattagg  10980
ctatgactgg gcacaacaga caatcggctg ctctgatgag ccgccagggt tttcccagtc  11040
```

acgacggatc cgaattcagc 11060

SEQ ID NO: 6 moltype = DNA length = 4384
FEATURE Location/Qualifiers
source 1..4384
mol_type = other DNA
organism = synthetic construct
SEQUENCE: 6
aggccctttc gtctcgcgcg tttcggtgat gacggtgaaa acctctgaca catgcagctc 60
ccggagacgg tcacagcttg tctgtaagcg gatgccggga gcagacaagc ccgtcagggc 120
gcgtcagcgg gtgttggcgg gtgtcggggc tggcttaact atgcggcatc agagcagatt 180
gtactgagag tgcaccatac cacagctttt caattcaatt catcattttt tttttattct 240
tttttttgat ttcggtttct ttgaaatttt tttgattcgg taatctccga acagaaggaa 300
gaacgaagga aggagcacag acttagattg gtatatatac gcatatgtag tgttgaagaa 360
acatgaaatt gcccagtatt cttaacccaa ctgcacagaa caaaaacctg caggaaacga 420
agataaatca tgtcgaaagc tacatataag gaacgtgctg ctactcatcc tagtcctgtt 480
gctgccaagc tatttaatat catgcacgaa aagcaaacaa acttgtgtgc ttcattggat 540
gttcgtacca ccaaggaatt actggagtta gttgaagcat taggtcccaa aatttgttta 600
ctaaaaacac atgtggatat cttgactgat ttttccatgg agggcacagt taagccgcta 660
aaggcattat ccgccaagta caattttttta ctcttcgaag acagaaaatt tgctgacatt 720
ggtaatacag tcaaattgca gtactctgcg ggtgtataca gaatagcaga atgggcagac 780
attacgaatg cacacggtgt ggtgggccca ggtattgtta gcggtttgaa gcaggcggca 840
gaagaagtaa caaaggaacc tagaggcctt ttgatgttag cagaattgtc atgcaagggc 900
tccctatcta ctggagaata tactaagggt actgttgaca ttgcgaagag cgacaaagat 960
tttgttatcg gctttattgc tcaaagagac atgggtggaa gagatgaagg ttacgattgg 1020
ttgattatga cacccggtgt gggtttagat gacaagggag acgcattggg tcaacagtat 1080
agaaccgtgg atgatgtggt ctctacagga tctgacatta ttattgttgg aagaggacta 1140
tttgcaaagg gaagggatgc taaggtagag ggtgaacgtt acagaaaagc aggctgggaa 1200
gcatatttga gaagatgcgg ccagcaaaac taaaaaactg tattataagt aaatgcatgt 1260
atactaaact cacaaattag agcttcaatt taattatatc agttattacc ctatgcggtg 1320
tgaaataccg cacagatgcg taaggagaaa ataccgcatc aggaaattgt aaacgttaat 1380
attttgttaa aattcgcgtt aaatttttgt taaatcagct cattttttaa ccaataggcc 1440
gaaatcggca aaatccctta taaatcaaaa gaatagaccg agatagggtt gagtgttgtt 1500
ccagtttgga acaagagtcc actattaaag aacgtggact ccaacgtcaa agggcgaaaa 1560
accgtctatc agggcgatgg cccactacgt gaaccatcac cctaatcaag ttttttgggg 1620
tcgaggtgcc gtaaagcact aaatcggaac cctaaaggga gcccccgatt tagagcttga 1680
cggggaaagc cggcgaacgt ggcgagaaag gaagggaaga aagcgaaagg agcgggcgct 1740
agggcgctgg caagtgtagc ggtcacgctg cgcgtaacca ccacacccgc cgcgcttaat 1800
gcgccgctac agggcgcgtc gcgccattcg ccattcaggc tgcgcaactg ttgggaaggg 1860
cgatcggtgc gggcctcttc gctattacgc cagctggcga aagggggatg tgctgcaagg 1920
cgattaagtt gggtaacgcc agggttttcc cagtcacgac gttgtaaaac gacggccagt 1980
gagcgcgcgt aatacgactc actatagggc gaattgggta ccgggccccc cctcgaggtc 2040
gacggtatcg ataagcttga tatcgaattc ctgcagcccg ggggatccac tagttctaga 2100
gcggccgcca ccgcggtgga gctccagctt ttgttccctt tagtgagggt taattgcgcg 2160
cttggcgtaa tcatggtcat agctgtttcc tgtgtgaaat tgttatccgc tcacaattcc 2220
acacaacata ggagccggaa gcataaagtg taaagcctgg ggtgcctaat gagtgaggta 2280
actcacatta attgcgttgc gctcactgcc cgctttccag tcgggaaacc tgtcgtgcca 2340
gctgcattaa tgaatcggcc aacgcgcggg gagaggcggt ttgcgtattg ggcgctcttc 2400
cgcttcctcg ctcactgact cgctgcgctc ggtcgttcgg ctgcggcgag cggtatcagc 2460
tcactcaaag gcggtaatac ggttatccac agaatcaggg gataacgcag gaaagaacat 2520
gtgagcaaaa ggccagcaaa aggccaggaa ccgtaaaaag gccgcgttgc tggcgttttt 2580
ccataggctc cgcccccctg acgagcatca caaaaatcga cgctcaagtc agaggtggcg 2640
aaacccgaca ggactataaa gataccaggc gtttccccct ggaagctccc tcgtgcgctc 2700
tcctgttccg accctgccgc ttaccggata cctgtccgcc tttctccctt cgggaagcgt 2760
ggcgctttct catagctcac gctgtaggta tctcagttcg gtgtaggtcg ttcgctccaa 2820
gctgggctgt gtgcacgaac cccccgttca gcccgaccgc tgcgccttat ccggtaacta 2880
tcgtcttgag tccaacccgg taagacacga cttatcgcca ctggcagcag ccactggtaa 2940
caggattagc agagcgaggt atgtaggcgg tgctacagag ttcttgaagt ggtggcctaa 3000
ctacggctac actagaagga cagtatttgg tatctgcgct ctgctgaagc cagttacctt 3060
cggaaaaaga gttggtagct cttgatccgg caaacaaacc accgctggta gcggtggttt 3120
ttttgtttgc aagcagcaga ttacgcgcag aaaaaaagga tctcaagaag atcctttgat 3180
cttttctacg gggtctgacg ctcagtggaa cgaaaactca cgttaaggga ttttggtcat 3240
gagattatca aaaaggatct tcacctagat ccttttaaat taaaaatgaa gttttaaatc 3300
aatctaaagt atatatgagt aaacttggtc tgacagttac caatgcttaa tcagtgaggc 3360
acctatctca gcgatctgtc tatttcgttc atccatagtt gcctgactcc ccgtcgtgta 3420
gataactacg atacgggagg gcttaccatc tggccccagt gctgcaatga taccgcgaga 3480
cccacgctca ccggctccag atttatcagc aataaaccag ccagccggaa gggccgagcg 3540
cagaagtggt cctgcaactt tatccgcctc catccagtct attaattgtt gccgggaagc 3600
tagagtaagt agttcgccag ttaatagttt gcgcaacgtt gttgccattg ctacaggcat 3660
cgtggtgtca cgctcgtcgt ttggtatggc ttcattcagc tccggttccc aacgatcaag 3720
gcgagttaca tgatccccca tgttgtgcaa aaaagcggtt agctccttcg gtcctccgat 3780
cgttgtcaga agtaagttgg ccgcagtgtt atcactcatg gttatggcag cactgcataa 3840
ttctcttact gtcatgccat ccgtaagatg cttttctgtg actggtgagt actcaaccaa 3900
gtcattctga gaatagtgta tgcggcgacc gagttgctct tgcccggcgt caatacggga 3960
taataccgcg ccacatagca gaactttaaa agtgctcatc attggaaaac gttcttcggg 4020
gcgaaaactc tcaaggatct taccgctgtt gagatccagt tcgatgtaac ccactcgtgc 4080
acccaactga tcttcagcat cttttacttt caccagcgtt tctgggtgag caaaaacagg 4140
aaggcaaaat gccgcaaaaa agggaataag ggcgacacgg aaatgttgaa tactcatact 4200
cttccttttt caatattatt gaagcattta tcagggttat tgtctcatga gcggatacat 4260

-continued

```
atttgaatgt atttagaaaa ataaacaaat aggggttccg cgcacatttc cccgaaaagt  4320
gccacctgac gtctaagaaa ccattattat catgacatta acctataaaa ataggcgtat  4380
cacg                                                               4384

SEQ ID NO: 7           moltype = DNA  length = 5407
FEATURE                Location/Qualifiers
source                 1..5407
                       mol_type = other DNA
                       organism = synthetic construct
SEQUENCE: 7
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatagcca tcctcatgaa aactgtgtaa cataataacc gaagtgtcga aaaggtggca  240
ccttgtccaa ttgaacacgc tcgatgaaaa aaataagata tatataaggt taagtaaagc  300
gtctgttaga aaggaagttt ttcctttttc ttgctctctt gtcttttcat ctactatttc  360
cttcgtgtaa tacagggtcg tcagatacat agatacaatt ctattacccc catccataca  420
atgccatctc atttcgatac tgttcaacta cacgccggcc aagagaaccc tggtgacaat  480
gctcacagat ccagagctgt accaatttac gccaccactt cttatgtttt cgaaaactct  540
aagcatggtt cgcaattgtt tggtctagaa gttccaggtt acgtctattc ccgtttccaa  600
aacccaacca gtaatgtttt ggaagaaaga attgctgctt tagaaggtgg tgctgctgct  660
ttggctgttt cctccggtca agccgctcaa acccttgcca tccaaggttt ggcacacact  720
ggtgacaaca tcgtttccac ttcttactta tacggtggta cttataacca gttcaaaatc  780
tcgttcaaaa gatttggtat cgaggctaga tttgttgaag gtgacaatcc agaagaattc  840
gaaaaggtct ttgatgaaag aaccaaggct gtttatttgg aaaccattgg taatccaaag  900
tacaatgttc cggattttga aaaaattgtt gcaattgctc acaaacacgg tattccagtt  960
gtcgttgaca acacatttgg tgccggtggt tacttctgtc agccaattaa atacggtgct  1020
gatattgtaa cacattctgc taccaaatgg attggtggtc atggtactac tatcggtggt  1080
attattgttg actctggtaa gttcccatgg aaggactacc cagaaaagtt ccctcaattc  1140
tctcaacctg ccgaaggata tcacggtact atctacaatg aagcctacgg taacttggca  1200
tacatcgttc atgttagaac tgaactatta agagatttgg gtccattgat gaacccattt  1260
gcctctttct tgctactaca aggtgttgaa acattatctt tgagagctga aagacacggt  1320
gaaaatgcat tgaagttagc caaatggtta gaacaatccc catacgtatc ttgggtttca  1380
taccctggtt tagcatctca ttctcatcat gaaaatgcta agaagtatct atctaacggt  1440
ttcggtggtg tcttatcttt cggtgtaaaa gacttaccaa atgccgacaa ggaaactgac  1500
ccattcaaac tttctggtgc tcaagttgtt gacaatttaa agcttgcctc taacttggcc  1560
aatgttggtg atgccaagac cttagtcatt gctccatact tcactaccca caaacaatta  1620
aatgacaaag aaaagttggc atctggtgtt accaaggact taattcgtgt ctctgttggt  1680
atcgaattta ttgatgacat tattgcagac ttccagcaat cttttgaaac tgttttcgct  1740
ggccaaaaac catgagtgtg cgtaatgagt tgtaaaatta tgtataaacc tactttctct  1800
cacaagttat gcggtgtgaa ataccgcaca gatgcgtaag gagaaaatac cgcatcagga  1860
aattgtaaac gttaatattt tgttaaaatt cgcgttaaat ttttgttaaa tcagctcatt  1920
ttttaaccaa taggccgaaa tcggcaaaat cccttataaa tcaaaagaat agaccgagat  1980
agggttgagt gttgttccag tttggaacaa gagtccacta ttaaagaacg tggactccaa  2040
cgtcaaaggg cgaaaaaccg tctatcaggg cgatggccca ctacgtgaac catcacccta  2100
atcaagtttt ttggggtcga ggtgccgtaa agcactaaat cggaacccta aagggagccc  2160
ccgatttaga gcttgacggg gaaagccggc gaacgtggcg agaaaggaag ggaagaaagc  2220
gaaaggagcg ggcgctaggg cgctggcaag tgtagcggtc acgctgcgcg taaccaccac  2280
acccgccgcg cttaatgcgc cgctacaggg cgcgtcgcgc cattcgccat tcaggctgcg  2340
caactgttgg gaagggcgat cggtgcgggc ctcttcgcta ttacgccagc tggcgaaagg  2400
gggatgtgct gcaaggcgat taagttgggt aacgccaggg ttttcccagt cacgacgttg  2460
taaaacgacg gccagtgagc gcgcgtaata cgactcacta tagggcgaat tgggtaccgg  2520
gccccccctc gaggtcgacg gtatcgataa gcttgatatc gaattcctgc agcccggggg  2580
atccactagt tctagagcgg ccgccaccgc ggtggagctc cagcttttgt tccctttagt  2640
gagggttaat tgcgcgcttg gcgtaatcat ggtcatagct gtttcctgtg tgaaattgtt  2700
atccgctcac aattccacac aacatacgag ccggaagcat aaagtgtaaa gcctggggtg  2760
cctaatgagt gagctaactc acattaattg cgttgcgctc actgcccgct ttccagtcgg  2820
gaaacctgtc gtgccagctg cattaatgaa tcggccaacg cgcggggaga ggcggtttgc  2880
gtattgggcg ctcttccgct tcctcgctca ctgactcgct gcgctcggtc gttcggctgc  2940
ggcgagcggt atcagctcac tcaaaggcgg taatacggtt atccacagaa tcaggggata  3000
acgcaggaaa gaacatgtga gcaaaaggcc agcaaaaggc caggaaccgt aaaaaggccg  3060
cgttgctggc gtttttccat aggctccgcc cccctgacga gcatcacaaa aatcgacgct  3120
caagtcagag gtggcgaaac ccgacaggac tataaagata ccaggcgttt ccccctggaa  3180
gctccctcgt gcgctctcct gttccgaccc tgccgcttac cggatacctg tccgcctttc  3240
tcccttcggg aagcgtggcg ctttctcata gctcacgctg taggtatctc agttcggtgt  3300
aggtcgttcg ctccaagctg ggctgtgtgc acgaaccccc cgttcagccc gaccgctgcg  3360
ccttatccgg taactatcgt cttgagtcca acccggtaag acacgactta tcgccactgg  3420
cagcagccac tggtaacagg attagcagag cgaggtatgt aggcggtgct acagagttct  3480
tgaagtggtg gcctaactac ggctacacta gaaggacagt atttggtatc tgcgctctgc  3540
tgaagccagt taccttcgga aaaagagttg gtagctcttg atccggcaaa caaaccaccg  3600
ctggtagcgg tggttttttt gtttgcaagc agcagattac gcgcagaaaa aaaggatctc  3660
aagaagatcc tttgatcttt tctacggggt ctgacgctca gtggaacgaa aactcacgtt  3720
aagggatttt ggtcatgaga ttatcaaaaa ggatcttcac ctagatcctt ttaaattaaa  3780
aatgaagttt taaatcaatc taaagtatat atgagtaaac ttggtctgac agttaccaat  3840
gcttaatcag tgaggcacct atctcagcga tctgtctatt tcgttcatcc atagttgcct  3900
gactccccgt cgtgtagata actacgatac gggagggctt accatctggc cccagtgctg  3960
caatgatacc gcgagaccca cgctcaccgg ctccagattt atcagcaata aaccagccag  4020
ccggaagggc cgagcgcaga agtggtcctg caactttatc cgcctccatc cagtctatta  4080
attgttgccg ggaagctaga gtaagtagtt cgccagttaa tagtttgcgc aacgttgttg  4140
```

-continued

```
ccattgctac aggcatcgtg gtgtcacgct cgtcgtttgg tatggcttca ttcagctccg  4200
gttcccaacg atcaaggcga gttacatgat cccccatgtt gtgcaaaaaa gcggttagct  4260
ccttcggtcc tccgatcgtt gtcagaagta agttggccgc agtgttatca ctcatggtta  4320
tggcagcact gcataattct cttactgtca tgccatccgt aagatgcttt tctgtgactg  4380
gtgagtactc aaccaagtca ttctgagaat agtgtatgcg gcgaccgagt tgctcttgcc  4440
cggcgtcaat acgggataat accgcgccac atagcagaac tttaaaagtg ctcatcattg  4500
gaaaacgttc ttcggggcga aaactctcaa ggatcttacc gctgttgaga tccagttcga  4560
tgtaacccac tcgtgcaccc aactgatctt cagcatcttt tactttcacc agcgtttctg  4620
ggtgagcaaa aacaggaagg caaaatgccg caaaaaaggg aataagggcg acacggaaat  4680
gttgaatact catactcttc ctttttcaat attattgaag catttatcag ggttattgtc  4740
tcatgagcgg atacatattt gaatgtattt agaaaaataa acaaataggg gttccgcgca  4800
catttccccg aaaagtgcca cctgggtcct tttcatcacg tgctataaaa ataattataa  4860
tttaaatttt ttaatataaa tatataaatt aaaaatagaa agtaaaaaaa gaaattaaag  4920
aaaaaatagt ttttgttttc cgaagatgta aaagactcta gggggatcgc caacaaatac  4980
taccttttat cttgctcttc ctgctctcag gtattaatgc cgaattgttt catcttgtct  5040
gtgtagaaga ccacacacga aaatcctgtg attttacatt ttacttatcg ttaatcgaat  5100
gtatatctat ttaatctgct tttcttgtct aataaatata tatgtaaagt acgctttttg  5160
ttgaaatttt ttaaaccttt gtttattttt ttttcttcat tccgtaactc ttctaccttc  5220
tttatttact ttctaaaatc caaatacaaa acataaaaat aaataaacac agagtaaatt  5280
cccaaattat tccatcatta aaagatacga ggcgcgtgta agttacaggc aagcgatccg  5340
tcctaagaaa ccattattat catgacatta acctataaaa ataggcgtat cacgaggccc  5400
tttcgtc                                                            5407

SEQ ID NO: 8           moltype = DNA  length = 3006
FEATURE                Location/Qualifiers
source                 1..3006
                       mol_type = other DNA
                       organism = synthetic construct
SEQUENCE: 8
attgaatatc acgcttaata aaggagaata aatcgttttc tactttcttc tgctgctata  60
ataagcacct atgggatcta tatagtattt ttataacgat agactttata aaagaaaata  120
cctaagtgaa aatttggtga attttgagat aattgttggg attccatttt taataaggca  180
ataaatattag gtatgtagaa tatactagaa gttctcctcg aggatttagg aatccataaa  240
agggaatctg caattctaca caattctata aatattatta tcatcgtttt atatgttaat  300
attcattgat cctattacat tatcaatcct tgcgtttcag cttccactaa tttagatgac  360
tatttctcat catttgcgtc atcttctaac accgtatatg ataatatact agtaacgtaa  420
atactagtta gtagatgata gttgattttt attccaacac taagaaataa tttcgccatt  480
tcttgaatgt atttaaagat atttaatgct ataatagaca tttaaatcca attcttccaa  540
catacaatgg gagtttggcc gagtggttta aggcgtcaga tttaggtgga tttaacctct  600
aaaatctctg atatcttcgg atgcaagggt tcgaatccct tagctctcag acatggaggc  660
ccagaatacc ctccttgaca gtcttgacgt gcgcagctca ggggcatgat gtgactgtcg  720
cccgtacatt tagcccatac atccccatgt ataatcattt gcatccatac attttgatgg  780
ccgcacggcg cgaagcaaaa attacggctc ctcgctgcag acctgcgagc agggaaacgc  840
tcccctcaca gacgcgttga attgtcccca cgccgcgccc ctgtagagaa atataaaagg  900
ttaggatttg ccactgaggt tcttctttca tatacttcct tttaaaatct tgctaggata  960
cagttctcac atcacatccg aacataaaca accatgggta aggaaaagac tcacgtttcg  1020
aggccgcgat taaattccaa catggatgct gatttatatg ggtataaatg ggctcgcgat  1080
aatgtcgggc aatcaggtgc gacaatctat cgattgtatg ggaagcccga tgcgccagag  1140
ttgtttctga aacatggcaa aggtagcgtt gccaatgatg ttacagatga gatggtcaga  1200
ctaaactggc tgacggaatt tatgcctctt ccgaccatca agcattttat ccgtactcct  1260
gatgatgcat ggttactcac cactgcgatc cccggcaaaa cagcattcca ggtattagaa  1320
gaatatcctg attcaggtga aaatattgtt gatgcgctgg cagtgttcct gcgccggttg  1380
cattcgattc ctgtttgtaa ttgtcctttt aacagcgatc gcgtatttcg tctcgctcag  1440
gcgcaatcac gaatgaataa cggtttggtt gatgcgagtg attttgatga cgagcgtaat  1500
ggctggcctg ttgaacaagt ctggaaagaa atgcataagc ttttgccatt ctcaccggat  1560
tcagtcgtca ctcatggtga tttctcactt gataacctta tttttgacga ggggaaatta  1620
ataggttgta ttgatgttgg acgagtcgga atcgcagacc gataccagga tcttgccatc  1680
ctatggaact gcctcggtga gttttctcct tcattacaga aacggctttt tcaaaaatat  1740
ggtattgata atcctgatat gaataaattg cagtttcatt tgatgctcga tgagtttttc  1800
taatcagtac tgacaataaa aagattcttg ttttcaagaa cttgtcattt gtatagtttt  1860
tttatattgt agttgttcta ttttaatcaa atgttagcgt gatttatatt ttttttcgcc  1920
tcgacatcat ctgcccagat gcgaagttaa gtgcgcagaa agtaatatca tgcgtcaatc  1980
gtatgtgaat gctggtcgct atactggtgt gcgtaatgag ttgtaaaatt atgtataaac  2040
ctactttctc tcacaagtac tatactttta taaaacgaac tttattgaaa tgaatatcct  2100
tttttttccct tgttacatgt cgtgactcgt actttgaacc taaattgttc taacatcaaa  2160
gaacagtgtt aattcgcagt cgagaagaaa aatatggtga acaagactca tctacttcat  2220
gagactactt tacgcctcct ataaagctgt cacactggat aaatttattg taggaccaag  2280
ttacaaaaga ggatgatgga ggtttcttta caataaagaa gcacatgtgt gttaacgttt  2340
ttagtatttg cttgttatgt aaatcaggaa aacttcgcgg gatttggttg gatgctactt  2400
tccatacaat aaatattata gatctaaaaa gccaaattac aagtaaagat tagtaaagct  2460
gttggaattc catcgttgat aaaaatgtta gttattaaat ataaaagtca gaataggtga  2520
acttggattt aattgttggc atttcgttgc tgctagaggc cataatatta gatagccagg  2580
acatactagt tctcctcgtg gtataggaat ccataaaatg gaattggtga ttctatgtga  2640
tatattcaca ttcttactac attatcaatc cttgcacttc agcttcctct aacctcgatg  2700
acatcttctc ataacttatg tcatcatcta acgccgtcta ttataatata ttgatagtat  2760
aagtattagt tgatagacaa tagtggattt ttattccaac agtgtctttg ttcgtctcag  2820
atatagtcgg attgcccttt taagcaatca atagtgtttt atttgcaaca atgtcgtcat  2880
agtttaatat gtcctataag atgttaactt gctcaacatt caacaaagtt tggtctcttg  2940
gcccagttgg ttaaggcacc gtgctaataa cgcggggatc agcggttcga tcccgctaga  3000
```

```
gaccat                                                            3006

SEQ ID NO: 9            moltype = DNA  length = 60
FEATURE                 Location/Qualifiers
source                  1..60
                        mol_type = other DNA
                        organism = synthetic construct
SEQUENCE: 9
gatatcttcg gatgcaaggg ttcgaatccc ttagctctca gacatggagg cccagaatac  60

SEQ ID NO: 10           moltype = DNA  length = 60
FEATURE                 Location/Qualifiers
source                  1..60
                        mol_type = other DNA
                        organism = synthetic construct
SEQUENCE: 10
aagtaggttt atacataatt ttacaactca ttacgcacac cagtatagcg accagcattc  60

SEQ ID NO: 11           moltype = DNA  length = 20
FEATURE                 Location/Qualifiers
source                  1..20
                        mol_type = other DNA
                        organism = synthetic construct
SEQUENCE: 11
actgccgagc agcttgttat                                              20

SEQ ID NO: 12           moltype = DNA  length = 20
FEATURE                 Location/Qualifiers
source                  1..20
                        mol_type = other DNA
                        organism = synthetic construct
SEQUENCE: 12
cacaacacga ggtacgggaa                                              20

SEQ ID NO: 13           moltype = DNA  length = 21
FEATURE                 Location/Qualifiers
source                  1..21
                        mol_type = other DNA
                        organism = synthetic construct
SEQUENCE: 13
gccatccgcc ccatctaata a                                            21

SEQ ID NO: 14           moltype = DNA  length = 20
FEATURE                 Location/Qualifiers
source                  1..20
                        mol_type = other DNA
                        organism = synthetic construct
SEQUENCE: 14
ccttccacga gcaaaacacg                                              20

SEQ ID NO: 15           moltype = DNA  length = 20
FEATURE                 Location/Qualifiers
source                  1..20
                        mol_type = other DNA
                        organism = synthetic construct
SEQUENCE: 15
gagggtggtt cgtcacattt                                              20

SEQ ID NO: 16           moltype = DNA  length = 19
FEATURE                 Location/Qualifiers
source                  1..19
                        mol_type = other DNA
                        organism = synthetic construct
SEQUENCE: 16
taccgccact gcctatgtt                                               19
```

METHOD FOR SYNTHESIS, ASSEMBLY AND FUNCTION TEST OF ARTIFICIAL CHLOROPLAST GENOME OF *Chlamydomonas reinhardtii*

REFERENCE TO A SEQUENCE LISTING

In accordance with 37 CFR § 1.831, the present specification makes reference to a Sequence Listing submitted electronically as a .xml file named "230067-AI-237-US-Sequence listing.xml". The .xml file is created on Oct. 8, 2023, and is 39,217 bytes in size. The entire contents of the Sequence Listing are hereby incorporated by reference.

FIELD

The present invention relates to the field of synthetic biology, in particular, to a method for synthesis, assembly and function test of an artificial chloroplast genome of *Chlamydomonas reinhardtii.*

BACKGROUND

*Chlamydomonas reinhardtii* is a single-cell eukaryotic algal model organism, which has three sets of genetic systems including nuclear genome, mitochondrial genome and chloroplast genome, and is often used to study the mechanisms of photosynthesis. With the establishment of genetic transformation technology for the genomes of *Chlamydomonas reinhardtii*, it is also widely used as a cell factory to produce recombinant proteins including vaccines, antibodies, drugs, and so on. As a type of microalgae, *Chlamydomonas reinhardtii* is widely used in the production of biodiesel due to its high carbohydrate and lipid contents, which has broad application prospects. However, the genetic manipulation system of *Chlamydomonas reinhardtii* is not yet fully mature. Based on existing research results, from the perspective of production of recombinant proteins, the presence of position effect and gene silencing in the nuclear genetic system can lead to lower production of recombinant proteins, thereby limiting the application of the nuclear genetic system. Relative to cell nucleus, the chloroplast genome is prokaryotic and relatively simple, thus chloroplast become the main research target for production of recombinant proteins. An artificial chloroplast genome of *Chlamydomonas reinhardtii* has a length of 205 kb, exists in a closed loop manner, contains a total of 99 genes, mainly including genes involved in photosynthesis, transcription, tRNA and rRNA, and the like. In addition to two large-segment inverted repetitive sequences of approximately 22 kb, there are still over 20% of short repetitive sequences distributed between genes in a scattered manner. In addition, the AT content in the chloroplast genome sequence is as high as 65%.

Conventional genetic engineering techniques are merely limited to allowing modifications to existing sequences. Therefore, it will be very meaningful to have the ability to significantly alter and arrange genetic content beyond conventional technical abilities. Therefore, there is a demand for synthetic genomes. Synthetic genomics is the total chemical de novo synthesis of the whole genome or most genomes through a series of technical means. Genome sequences such as yeast alanine tRNA gene and poliovirus, φX174 phage, T7 phage, SARS-like coronavirus and West Nile fever virus have been artificially modified and synthesized successively. The most representative work is the synthesis and minimization of *Mycoplasma mycoides* genomes, the recoding of

*Escherichia coli* genomes and the artificial synthesis of *Saccharomyces cerevisiae* chromosomes. The total chemical de novo of a plastid genome is limited to the complete assembly of the rice chloroplast genome by chemically synthesized segments in *Bacillus subtilis*, but function analysis of the synthesized rice chloroplast genome has not been conducted. In 2012, a *Chlamydomonas reinhardtii* chloroplast genome was re-assembled in yeast through large segments of the BAC library derived from *Chlamydomonas reinhardtii* chloroplast genome, achieving synchronous modification of multiple sites within the *Chlamydomonas* chloroplast genome.

However, so far, the de novo design and in vitro assembly of the chloroplast genome and the functionalization of chloroplast genome synthesis in algae cells have not been achieved. Therefore, the prior art still needs improvement.

SUMMARY

In view of the defects of the prior art, the present invention provides a method for synthesis, assembly and function test of an artificial chloroplast genome of *Chlamydomonas reinhardtii*. By using totally chemically synthesized artificial chloroplast genome segments, total chemical de novo synthesis and assembly of a chloroplast genome are achieved in a yeast-bacterium system, which provides a new solution for the rational design, modification and reconstruction of a photosynthetic system of photosynthetic organisms, improvement of photosynthetic efficiency of crops, and solving of agricultural crisis such as food security.

The present invention has the following technical solution:

Provided is a method for synthesis, assembly and function test of an artificial chloroplast genome of *Chlamydomonas reinhardtii*, the method including de novo design, total chemical synthesis, assembly and function verification of an artificial chloroplast genome of *Chlamydomonas reinhardtii*, wherein a nucleotide sequence of the artificial chloroplast genome of *Chlamydomonas reinhardtii* is obtained by designing and modifying a nucleotide sequence of a wild-type *Chlamydomonas reinhardtii* chloroplast genome and adding a BAC vector backbone, a streptomycin resistance gene aadA, a paromomycin resistance gene aphVIII and an HA tag.

According to the method for synthesis, assembly and function test of an artificial chloroplast genome of *Chlamydomonas reinhardtii*, the nucleotide sequence of the artificial chloroplast genome of *Chlamydomonas reinhardtii* has a full length of 221,372 bp.

According to the method for synthesis, assembly and function test of an artificial chloroplast genome of *Chlamydomonas reinhardtii*, the artificial chloroplast genome of *Chlamydomonas reinhardtii* is divided into 44 primary segments after being de novo designed, each of the primary segments have 120 bp homologous recombination sequences at two ends.

According to the method for synthesis, assembly and function test of an artificial chloroplast genome of *Chlamydomonas reinhardtii*, the primary segments are all synthesized through a chemical method.

According to the method for synthesis, assembly and function test of an artificial chloroplast genome of *Chlamydomonas reinhardtii*, the BAC vector backbone has a length of 11,060 bp, and an insertion site is located at 205,535 bp of the wild-type *Chlamydomonas reinhardtii* chloroplast genome; the streptomycin resistance gene aadA has a length of 1,630 bp, and an insertion site is located between 173,174 bp and 173,175 bp of the wild-type *Chlamydomonas reinhardtii* chloroplast genome; the paromomycin resistance gene aphVIII has a length of 2,287 bp, and an insertion site is located between 71,064 bp and 71,065 bp of the wild-type *Chlamydomonas reinhardtii* chloroplast genome; a 3×HA-1 tag is located behind atpI, and an insertion site is located between 170,786 bp and 170,787 bp of the wild-type *Chlamydomonas reinhardtii* chloroplast genome; a 3×HA-2 tag is located behind rps4, and an insertion site is located between 33,292 bp and 33293 bp of the wild-type *Chlamydomonas reinhardtii* chloroplast genome.

According to the method for synthesis, assembly and function test of an artificial chloroplast genome of *Chlamydomonas reinhardtii*, the synthesis and assembly of the artificial chloroplast genome of *Chlamydomonas reinhardtii* includes the following steps:

- 6.1 connecting the 44 primary segments of the de novo designed artificial chloroplast genome of *Chlamydomonas reinhardtii* to the pUC18 vector, respectively;
- 6.2 co-transforming a BAC vector segment, a screening marker segment, a 7-35 bridging segment, a seg44 segment, segments seg35-seg43, a seg1 segment, and segments seg3-seg7 into yeast strain BY4741, and screening by using the screening medium SC-URA to obtain the yeast strain −1 containing an intermediate plasmid 1;
- 6.3 co-transforming a pRS415 vector segment and segments seg7-seg21 into yeast strain BY4742, screening by using a screening medium SC-LEU, using a kanMX segment to replace the Met gene on a genome with a yeast strain obtained by screening for Met knockout, and using an SC-LEU+G418 medium for screening to obtain a yeast strain −2 containing an intermediate plasmid 2;
- 6.4 co-transforming a pRS411 vector segment and segments seg22-seg35 into yeast strain BY4741, and using a screening medium SC-MET for screening to obtain a yeast strain −3 containing an intermediate plasmid 3;
- 6.5 hybridizing the yeast strain −2 and the yeast strain −3, and screening through an SC-LEU-MET plate; then carrying out spore production and spore division, and screening through an SC-LEU plate and an SC-MET plate; then hybridizing with a yeast SZU-JDY19 and a yeast SZU-JDY20; then hybridizing with the yeast strain −1 containing the intermediate plasmid 1, and screening through an SC-LEU-MET-URA plate; transforming an SZU-ZLP012 plasmid of a strain obtained by screening, and screening through an SC-URA-LEU-MET-HIS plate;
- 6.6 inducing I-SceI gene expression in the SZU-ZLP012 plasmid by using a galactose, cleaving an I-SceI site to linearize 3 intermediate plasmids, and then obtaining a yeast strain containing a complete artificial chloroplast genome of *Chlamydomonas reinhardtii* through homologous recombination in a yeast cell.

According to the method for synthesis, assembly and function test of an artificial chloroplast genome of *Chlamydomonas reinhardtii*, a nucleotide sequence of the intermediate plasmid 1 has a full length of 92,477 bp and contains nucleotide sequences of 1-33,292 bp and 159,554 bp-205,535 bp of the wild-type *Chlamydomonas reinhardtii* chloroplast genome, and a BAC backbone sequence is added at 205,535 bp of the wild-type *Chlamydomonas reinhardtii* chloroplast genome; a nucleotide sequence of the intermediate plasmid 2 has a full length of 81,426 bp and contains nucleotide sequences of 28,513 bp-102,566 bp of the wild-type *Chlamydomonas reinhardtii* chloroplast genome, and pRS406 vector sequences are connected at head and tail interfaces of genome nucleotide sequences; a nucleotide sequence of the intermediate plasmid 3 has a full length of 72,377 bp and contains nucleotide sequences of 97,668 bp-164,450 bp of the wild-type *Chlamydomonas reinhardtii* chloroplast genome, and pRS411 vector sequences are connected at head and tail interfaces of genome nucleotide sequences.

According to the method for synthesis, assembly and function test of an artificial chloroplast genome of *Chlamydomonas reinhardtii*, the function test of the artificial chloroplast genome of *Chlamydomonas reinhardtii* includes the following steps:

- 8.1 transferring the artificial chloroplast genome of *Chlamydomonas reinhardtii* into chloroplast of *Chlamydomonas reinhardtii* CC5168 by particle bombardment, and obtaining positive transformants by streptomycin screening, PCR and Southern Blot screening;
- 8.2 carrying out homogenization screening on the positive transformants by using gradient streptomycin resistance concentration;
- 8.3 carrying out Western Blot experiment on the positive transformants for verification of protein expression; and detecting the growth curve of and photosynthesis of the positive transformants.

According to the method for synthesis, assembly and function test of an artificial chloroplast genome of *Chlamydomonas reinhardtii*, detection segments for screening of the positive transformants are aphVIII, BAC-seg44, and BAC-seg1, respectively.

According to the method for synthesis, assembly and function test of an artificial chloroplast genome of *Chlamydomonas reinhardtii*, a probe used for Southern Blot verification of the positive transformants is obtained by amplification of aphVIII-F1/R1 and psaA-F/R primers, nucleotide sequences of the aphVIII-F1/R1 primer being shown in SEQ ID NO.1 and SEQ ID NO.2, and nucleotide sequences of the psaA-F/R primer being shown in SEQ ID NO.3 and SEQ ID NO.4.

Beneficial effects are as follows: the present invention provides a method for synthesis, assembly and function test of an artificial chloroplast genome of *Chlamydomonas reinhardtii*. According to the present invention, rational design has been carried out on the *Chlamydomonas reinhardtii* chloroplast genome for the first time, and total artificial synthesis of the *Chlamydomonas reinhardtii* chloroplast genome is proposed. By using the method of synthetic biology, all nucleic acid segments are constructed from chemically synthesized nucleic acid sequences. By using totally chemically synthesized chloroplast genome segments, total chemical de novo synthesis and assembly of a chloroplast genome are achieved in a yeast-bacterium system. Then, a totally chemically synthesized chloroplast genome is transformed into *Chlamydomonas* cells to replace the original chloroplast genome through various technical means, which works normally, and has been verified, fulfilling biological functions of the totally chemically synthesized chloroplast genome. The method can be widely applied in gene editing of the *Chlamydomonas reinhardtii* chloroplast genome and production of antibody drugs and the like, and has huge commercial advantages and broad market prospects. Meanwhile, according to the present invention, the *Chlamydomonas reinhardtii* chloroplast genome is an efficient platform for carrying out synthetic biology operation, the de novo design, total chemical synthesis, in vitro assembly and identification of the genome thereof provide a new solution for the rational design, modification and reconstruction of a photosynthetic system of photosynthetic organisms, improvement of photosynthetic efficiency of crops, and solving of agricultural crisis such as food security.

DETAILED DESCRIPTION OF THE EMBODIMENTS

The present invention provides a method for synthesis, assembly and function test of an artificial chloroplast genome of *Chlamydomonas reinhardtii*. In order to make the purpose, technical solution, and effects of the present invention clearer and more explicit, the present invention is further illustrated in detail below. It should be understood that the specific embodiments described herein are only used to explain the present invention, but not to limit the present invention.

An embodiment of the present invention provides a method for synthesis, assembly and function test of an artificial chloroplast genome of *Chlamydomonas reinhardtii*, the method including de novo design, total chemical synthesis, assembly and function verification of an artificial chloroplast genome of *Chlamydomonas reinhardtii*. According to the embodiment of the present invention, by adopting the method of synthetic biology, by using totally chemically synthesized chloroplast genome segments, total chemical de novo synthesis and assembly of a chloroplast genome are achieved in a yeast-bacterium system. Then, a totally chemically synthesized chloroplast genome is transformed into *Chlamydomonas* cells to replace the original chloroplast genome through various technical means, fulfilling biological functions of the totally chemically synthesized chloroplast genome.

Figure 1:
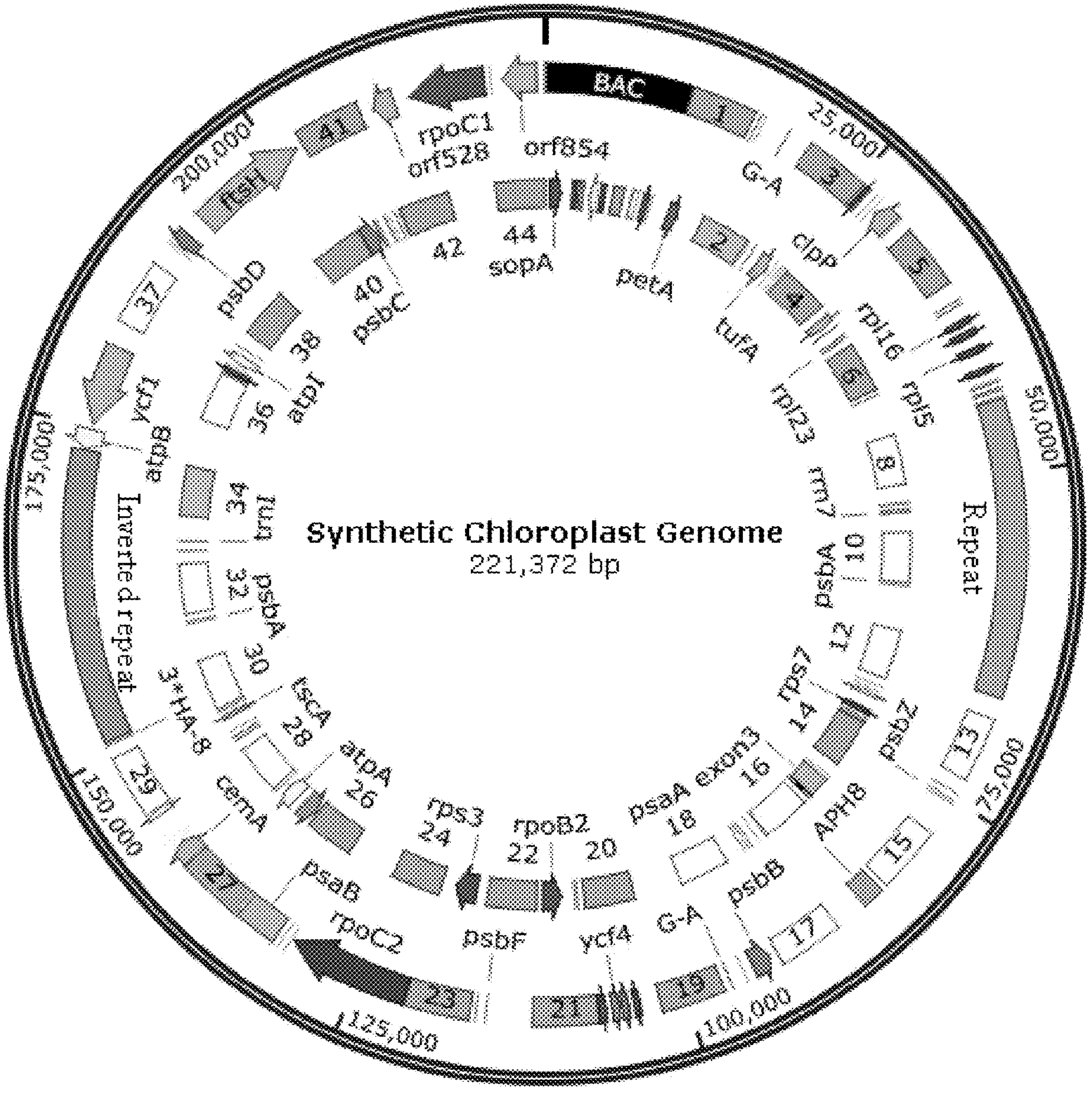
FIG. 1 is a map of an artificial chloroplast genome of *Chlamydomonas reinhardtii* provided by an embodiment of the present invention.

In some implementations, a nucleotide sequence of the artificial chloroplast genome of *Chlamydomonas reinhardtii* is obtained by designing and modifying a nucleotide sequence of a wild-type *Chlamydomonas reinhardtii* chloroplast genome and adding a BAC vector backbone, a streptomycin resistance gene aadA, a paromomycin resistance gene aphVIII and an HA tag. The finally designed and obtained artificial chloroplast genome of *Chlamydomonas reinhardtii* is shown in FIG. 1.

In some implementations, the nucleotide sequence of the artificial chloroplast genome of *Chlamydomonas reinhardtii* has a total of 221.372 bp bases.

In some implementations, the nucleotide sequence of the wild-type *Chlamydomonas reinhardtii* chloroplast genome has a full length of 205,535 bp, with NCBI Sequence Number of NC_005353.1.

In some implementations, the artificial chloroplast genome of *Chlamydomonas reinhardtii* is divided into 44 primary segments when being de novo designed, each of the primary segments having 120 bp homologous recombination sequences at two ends. Distribution of the 44 primary segments is shown in FIG. 1.

In some implementations, the primary segments are all synthesized through a chemical method. All the primary segments are connected to a pUC18 vector. Meanwhile, the primary segments can also be obtained by digestion on the vector by a restriction enzyme Not I.

In some implementations, the BAC vector backbone, aphVIII and aadA resistance screening markers, and the HA tag are added to the artificial chloroplast genome of *Chlamydomonas reinhardtii.*

In some implementations, the BAC vector backbone has a length of 11,060 bp, and an insertion site is located at 205,535 bp of the wild-type *Chlamydomonas reinhardtii* chloroplast genome; the streptomycin resistance gene aadA has a length of 1,630 bp, and an insertion site is located between 173,174 bp and 173,175 bp of the wild-type *Chlamydomonas reinhardtii* chloroplast genome; the paromomycin resistance gene aphVIII has a length of 2,287 bp, and an insertion site is located between 71,064 bp and 71,065 bp of the wild-type *Chlamydomonas reinhardtii* chloroplast genome; a 3×HA-1 tag is located behind atpI, and an insertion site is located between 170,786 bp and 170,787 bp of the wild-type *Chlamydomonas reinhardtii* chloroplast genome; a 3×HA-2 tag is located behind rps4, and an insertion site is located between 33,292 bp and 33293 bp of the wild-type *Chlamydomonas reinhardtii* chloroplast genome.

In some implementations, the synthesis and assembly of the artificial chloroplast genome of *Chlamydomonas reinhardtii* includes the following steps:

S01, connecting the 44 primary segments of the de novo designed artificial chloroplast genome of *Chlamydomonas reinhardtii* to a pUC18 vector, respectively;

S02, co-transforming a BAC vector segment, a screening marker segment, a 7-35 bridging segment, a seg44 segment, segments seg35-seg43, a seg1 segment, and segments seg3-seg7 into a yeast BY4741, and screening by using a screening medium SC-URA to obtain a yeast strain −1 containing an intermediate plasmid 1;

S03, co-transforming a pRS415 vector segment and segments seg7-seg21 into a yeast BY4742, screening by using a screening medium SC-LEU, using a kanMX segment to replace a Met gene on a genome with a yeast strain obtained by screening for Met knockout, and using an SC-LEU+G418 medium for screening to obtain a yeast strain −2 containing an intermediate plasmid 2;

S04, co-transforming a pRS411 vector segment and segments seg22-seg35 into a yeast BY4741, and using a screening medium SC-MET for screening to obtain a yeast strain −3 containing an intermediate plasmid 3;

505, hybridizing the yeast strain −2 and the yeast strain −3, and screening through an SC-LEU-MET plate; then carrying out spore production and spore division, and screening through an SC-LEU plate and an SC-MET plate; then hybridizing with SZU-JDY19 (Preservation Number: CCTCC M 20221034) and SZU-JDY20 (Preservation Number: CCTCC M 20221033); then hybridizing with the yeast strain −1 containing the intermediate plasmid 1, and screening through an SC-LEU-MET-URA plate; transforming an SZU-ZLP012 plasmid (Preservation Number: CCTCC M 20221031) of a strain obtained by screening, and screening through an SC-URA-LEU-MET-HIS plate;

S06, inducing I-SceI gene expression in the SZU-ZLP012 plasmid by using galactose, cleaving an I-SceI site to linearize 3 intermediate plasmids, and then obtaining a yeast strain (Preservation Number: CCTCC M 20221035) containing a complete artificial chloroplast genome of *Chlamydomonas reinhardtii* through homologous recombination in a yeast cell.

Figure 2:
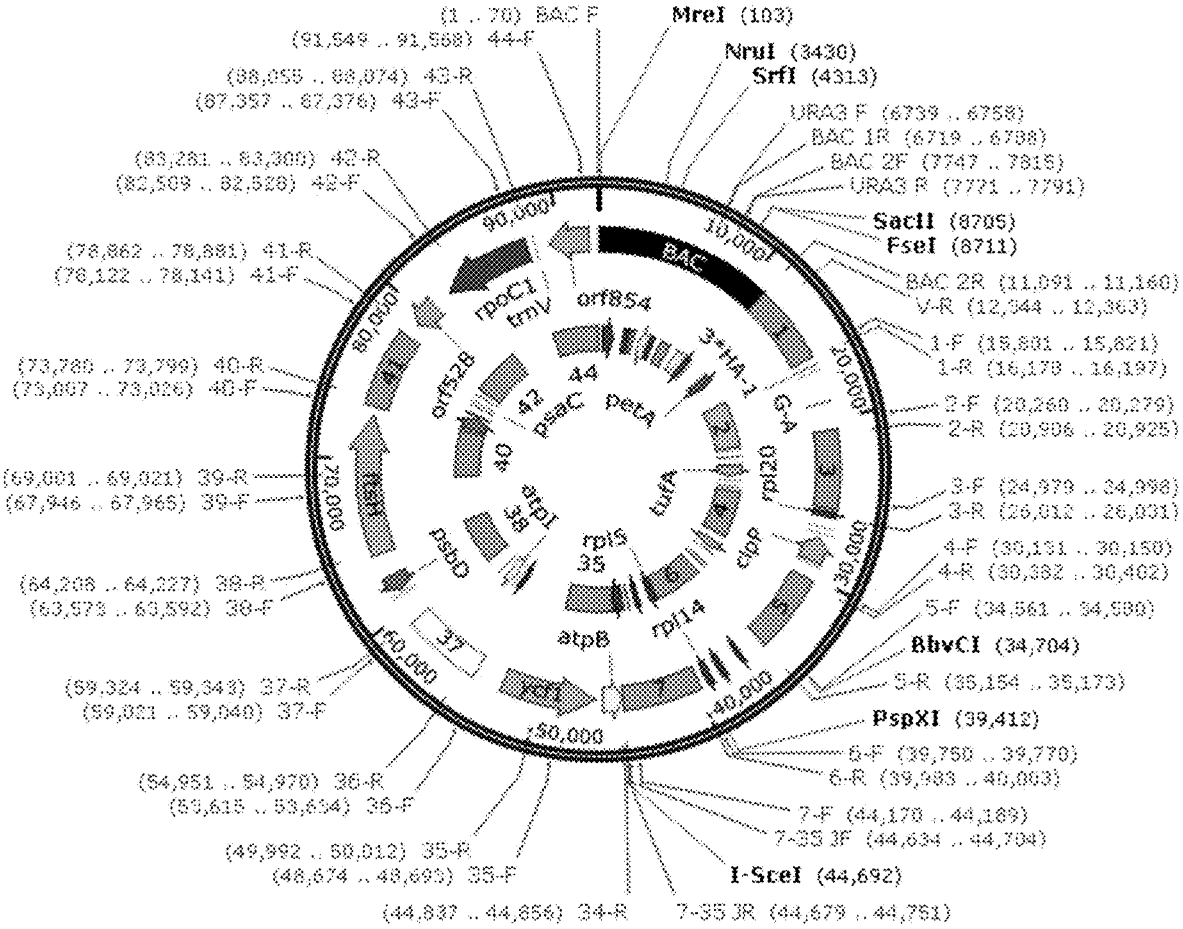
FIG. 2 is a map of an intermediate plasmid 1 provided by an embodiment of the present invention.

In some implementations, a nucleotide sequence of the intermediate plasmid 1 has a full length of 92,477 bp and contains nucleotide sequences of 1-33,292 bp and 159,554 bp-205,535 bp of the wild-type *Chlamydomonas reinhardtii* chloroplast genome, and a map thereof is shown in FIG. 2. A BAC backbone sequence is added at 205,535 bp of the wild-type *Chlamydomonas reinhardtii* chloroplast genome, and is shown in SEQ ID NO.5.

Figure 3:
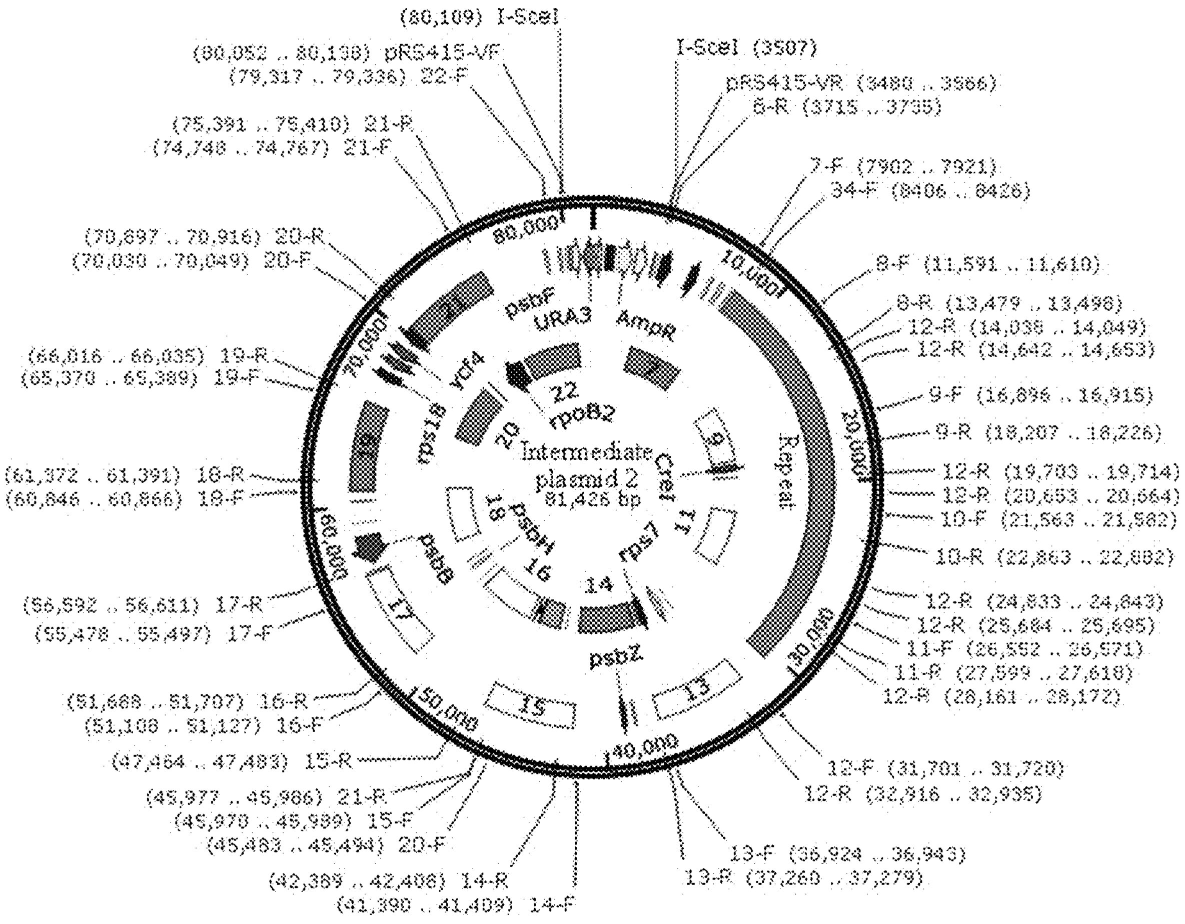
FIG. 3 is a map of an intermediate plasmid 2 provided by an embodiment of the present invention.

In some implementations, a nucleotide sequence of the intermediate plasmid 2 has a full length of 81,426 bp and contains nucleotide sequences of 28,513 bp-102,566 bp of the wild-type *Chlamydomonas reinhardtii* chloroplast genome, pRS406 vector sequences are connected at head and tail interfaces of genome nucleotide sequences, and a map thereof is shown in FIG. 3; the pRS406 vector sequences are shown in SEQ ID NO.6.

Figure 4:
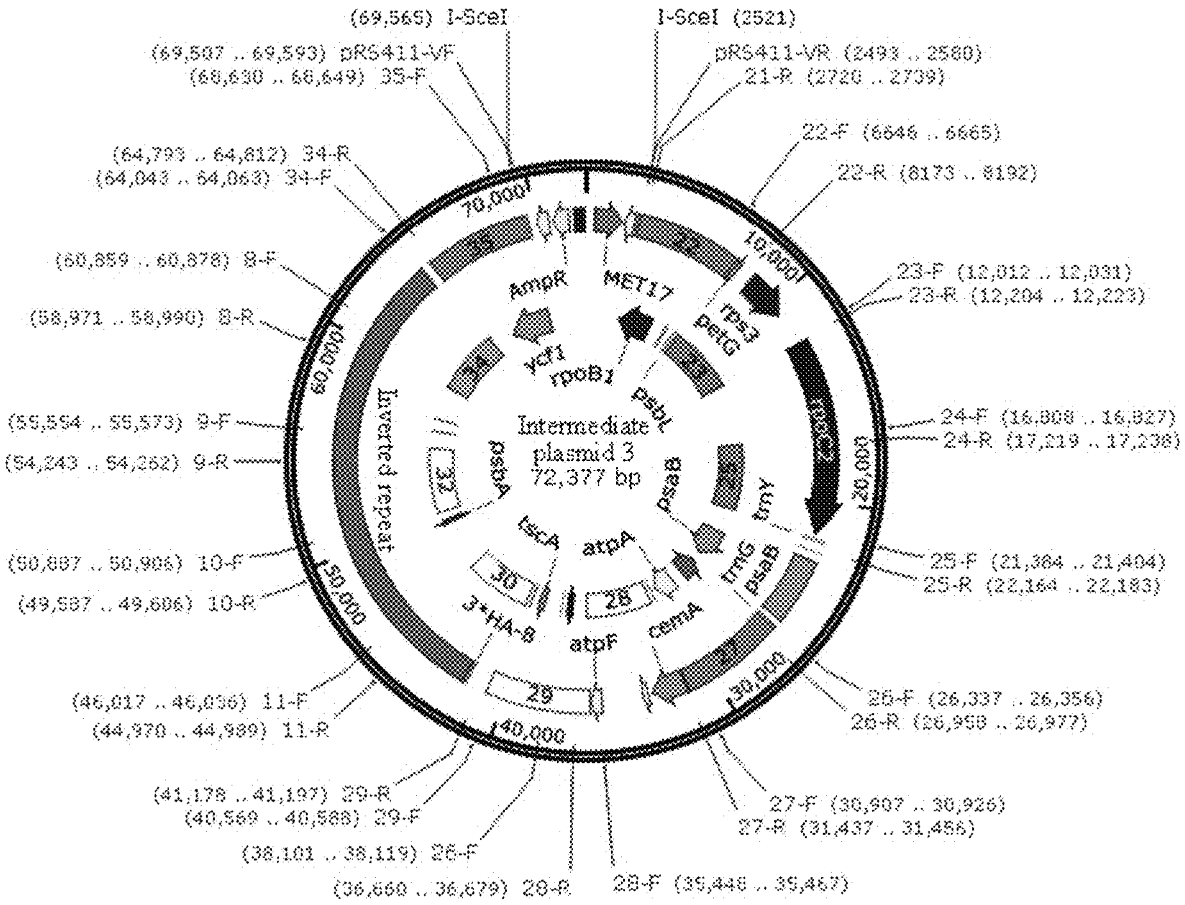
FIG. 4 is a map of an intermediate plasmid 3 provided by an embodiment of the present invention.

In some implementations, a nucleotide sequence of the intermediate plasmid 3 has a full length of 72,377 bp and contains nucleotide sequences of 97,668 bp-164,450 bp of the wild-type chloroplast genome, pRS411 vector sequences are connected at head and tail interfaces of genome nucleotide sequences, and a map thereof is shown in FIG. 4; the pRS411 vector sequence is shown in SEQ ID NO.7.

In some implementations, in step S03, a kanMX segment is used to replace a Met gene on a genome with a yeast strain obtained by screening for Met knockout; pFA6-kanMX4 (commercial plasmid, purchased from Shanghai Yaji Biotechnology Co., Ltd., Article Number: YC-14391RJ) is used as a template for PCR amplification by using a primer Met17F/R to obtain a kanMX segment, the pFA6-kanMX4 being purchased from a commercial company; PCR segments of kanMX are transformed into a yeast containing the intermediate plasmid 2, subjected to screening culture, and screened with SC-LEU+G418; a transformed plate is photocopied onto a plate of G418, and monoclones that can grow on both plates are selected, that is, screening is carried out to obtain the yeast strain −2.

Specifically, a sequence of the kanMX segment is shown in SEQ ID NO.8; sequences of primers Met17-F and Met17-R are shown in SEQ ID NO.9 and SEQ ID NO.10.

Specifically, a ZLP012 plasmid carries I-SceI endonuclease and HIS3 auxotrophic screening marker genes. The expression of I-SceI is induced by using the galactose, and chunk1 (intermediate plasmid 1), chunk2 (intermediate plasmid 2) and chunk3 (intermediate plasmid 3) linearize three intermediate plasmids in a yeast due to the cleavage of the I-SceI site.

According to the embodiment of the present invention, when the artificial chloroplast genome of *Chlamydomonas reinhardtii* is assembled, firstly, a vector segment is amplified by PCR to carry homologous sequences with both ends of segments; afterwards, the carrier segment and corresponding segments are co-transformed into yeast cells; then, screening is carried out by an appropriate auxotrophic SC screening medium to obtain transformants, genomes of yeast transformants are extracted, and correctly assembled chunk1, chunk2, and chunk3 are obtained by Junction PCR screening. An I-SceI endonuclease recognition site is added at each intermediate plasmid. After all secondary segments are introduced into a yeast, the intermediate plasmids are linearized by inducing the expression of I-SceI endonuclease in cells, and the three secondary segments are assembled into a final artificial synthetic chloroplast genome by using a homologous recombination mechanism.

In some implementations, the function test of the artificial chloroplast genome of *Chlamydomonas reinhardtii* includes the following steps:

S100, transferring the artificial chloroplast genome of *Chlamydomonas reinhardtii* into a chloroplast of *Chlamydomonas reinhardtii* CC5168 by particle bombardment, and obtaining positive transformants by streptomycin screening, PCR and Southern Blot screening;

S200, carrying out homogenization screening on the positive transformants by using gradient streptomycin resistance concentration;

S300, carrying out Western Blot experiment on the positive transformants for verification of protein expression; and detecting a growth curve of the positive transformants and photosynthesis of a repair mutant strain.

Specifically, a concentration of a streptomycin screening medium is 150 μg/mL. The homogenized gradient streptomycin concentrations are 150 μg/mL, 300 μg/mL, 400 μg/mL, 500 μg/mL, 600 μg/mL, 700 μg/mL, 800 μg/mL, 900 μg/mL and 1000 μg/mL.

During function analysis of the artificial chloroplast genome of *Chlamydomonas reinhardtii*, firstly, a yeast plasmid is extracted, and transferred into *Escherichia coli* EPI300 by electroporation, an *Escherichia coli* plasmid is extracted, a synthetic chloroplast genome is transferred into photo-deficient *Chlamydomonas reinhardtii* CC5168 (ΔpsbH) by biolistic transformation, and transformants are obtained through antibiotic screening and HS medium screening, PCR and Southern Blot positive screening are carried out on the transformants; Finally, Western Blot verification is carried out on the positive transformants, and meanwhile, the growth curve of the transformants and photosynthesis repair of photo-deficient algal strains are detected.

In some implementations, detection segments for identification and positive screening of the positive transformants are aphVIII, BAC-seg44, and BAC-seg1, respectively, and detection primers are aphVIII-F/R, BAC44-F/R, and BAC1-F/R, respectively; nucleotide sequences of the aphVIII-F/R are shown in SEQ ID NO.11 and SEQ ID NO.12, nucleotide sequences of the BAC44-F/R are shown in SEQ ID NO.13 and SEQ ID NO.14, and nucleotide sequences of the BAC1-F/R are shown in SEQ ID NO.15 and SEQ ID NO.16.

In some implementations, probes used for Southern Blot verification of the positive transformants are obtained by amplification of aphVIII-F1/R1 and psaA-F/R primers, nucleotide sequences of the aphVIII-F1/R1 primer are shown in SEQ ID NO.1 and SEQ ID NO.2, and nucleotide sequences of the psaA-F/R primer are shown in SEQ ID NO.3 and SEQ ID NO.4.

The embodiment of the present invention provides implementations and methods for the design, synthesis, assembly, and expression of synthetic genomes. Methods are included for: rational design of genomes; preparation of small nucleic acid segments and assembly of them into expression cassettes containing genomic components; correction of errors in expression cassette sequences; assembly of the expression cassettes into synthetic genomes (for example, through in vitro recombination); screening and verification of transferring of synthetic genomes into *Chlamydomonas reinhardtii* chloroplasts and positive transformed algae strains by using chloroplasts. The present invention includes methods for the rational design of synthetic genomes and construction of synthetic genomes, including preparation and assembly of genomic nucleic acid components, wherein all genomes are constructed from chemically synthesized nucleic acid components. In a specific implementation, a complete synthetic genome is constructed entirely from chemically synthesized nucleic acid components or copies of the chemically synthesized nucleic acid components. Further, the synthetic genome can be a synthetic organelle genome.

According to the present invention, by adopting the method of synthetic biology, by using totally chemically synthesized chloroplast genome segments, total chemical de novo synthesis and assembly of a chloroplast genome are achieved in a yeast-bacterium system. Then, a totally chemically synthesized chloroplast genome is transformed into *Chlamydomonas* cells to replace the original chloroplast genome through various technical means, fulfilling biological functions of the totally chemically synthesized chloroplast genome. According to the present invention, the *Chlamydomonas reinhardtii* chloroplast genome is an efficient platform for carrying out synthetic biology operation, the de novo design, total chemical synthesis, in vitro assembly and identification of the genome thereof provide a new solution for the rational design, modification and reconstruction of a photosynthetic system of photosynthetic organisms, improvement of photosynthetic efficiency of crops, and solving of agricultural crisis such as food security.

The method for synthesis, assembly and function test of an artificial chloroplast genome of *Chlamydomonas reinhardtii* of the present invention is further explained and illustrated below through specific embodiments.

Embodiment 1 Design of Artificial Chloroplast Genome of *Chlamydomonas reinhardtii*

The sequence (NC_005353.1) of a wild-type *Chlamydomonas reinhardtii* chloroplast genome was downloaded from NCBI, and designed based on a sequence of a wild-type chloroplast genome, including insertion of an HA tag to detect expression of a target protein, and insertion of two resistance gene expression boxes, 5'-atpA-aadA-rbcL-3' and 5'-atpA-aphVIII-rbcL-3', for subsequent screening. The 5'-atpA-aphVIII-rbcL-3' had a resistance screening marker length of 2,287 bp, located between 71,064 bp and 71,065 bp of the wild-type *Chlamydomonas reinhardtii* chloroplast genome. The aadA had a resistance screening marker length of 1,630 bp, located between 173,174 bp and 173,175 bp of the wild-type *Chlamydomonas reinhardtii* chloroplast genome. A 3×HA-1 tag was behind atpI, and between 170,786 bp and 170,787 bp. A 3×HA-2 tag was behind rps4, and between 33,292 bp and 33293 bp. Through de novo design, the sequence of the artificial chloroplast genome of *Chlamydomonas reinhardtii* with a full length of 221,372 bp was obtained, as shown in FIG. 1.

Embodiment 2 Assembly of Artificial Chloroplast Genome of *Chlamydomonas reinhardtii*

A commercial company was commissioned to synthesize all primary segments. All the primary segments were connected to a pUC18 vector and could be obtained by a restriction enzyme Not I. The above sequences were confirmed by sequencing and digestion.

1. Assembly of Intermediate Plasmid 1

Assembly was carried out in a BY4741 background strain (commercial strain, purchased from Huinuo Biomedical Technology Co., Ltd., Article Number: A226), with a total of 21 segments, including 17 chloroplast genome synthetic segments (including nucleotide sequences of 0-33,292 bp and 159,554 bp-205,535 bp of a wild-type chloroplast genome), 2 BAC segments, a URA3 screening gene, and a 7-35 bridging segment. BAC served as a vector for an intermediate plasmid 1, the URA3 gene provided an auxotrophic screening marker, and the 7-35 bridging segment was used for insertion of an I-SceI digestion site between segment 7 and segment 35. A map of the finally obtained intermediate plasmid 1 is shown in FIG. 2. A specific assembly process was as follows:

1) Segment preparation: synthetic segments 1-7 and 35-44 were obtained through Not I digestion, and by using a pRS416 plasmid (commercial plasmid, purchased from ACD, Article Number: 518681-C2) as a template, and using vecF+vecR as primers, through PCR amplification, a pRS416 vector segment with homologous sequences of segment a and segment d was obtained. The pRS416 amplified segment, seg-a, seg-b1, seg-b2, seg-c, and seg-d segments were co-transformed into a BY4741 yeast (commercial strain, purchased from Huinuo Biomedical Technology Co., Ltd., Article Number: A226), and screening was carried out by an SC-URA screening medium to obtain segment 2. By using pJS356 (pJS356 Cloned pTERM+415, DNA) as a template and using BAC F/1R and BAC 2F/2R as primers, through PCR amplification, BAC vector segments were obtained. By using pRS406 (publicly available plasmid, see Sikorski and Hieter, 1989) (pRS406-ua3, DNA) as a template and using URA3 F and URA3 R as primers, through PCR amplification, screening marker segments were obtained. 7-35 segments were obtained through 7-35 JF/JR Primer annealing, and segment seg44 was obtained through 44-V L/R PCR.

2) Yeast transformation: vector segments, seg35-seg43, seg1, and seg3-seg7 were co-transformed into a yeast BY4741, and screening was carried out by using a screening medium SC-URA to obtain transformants.

Figure 5:
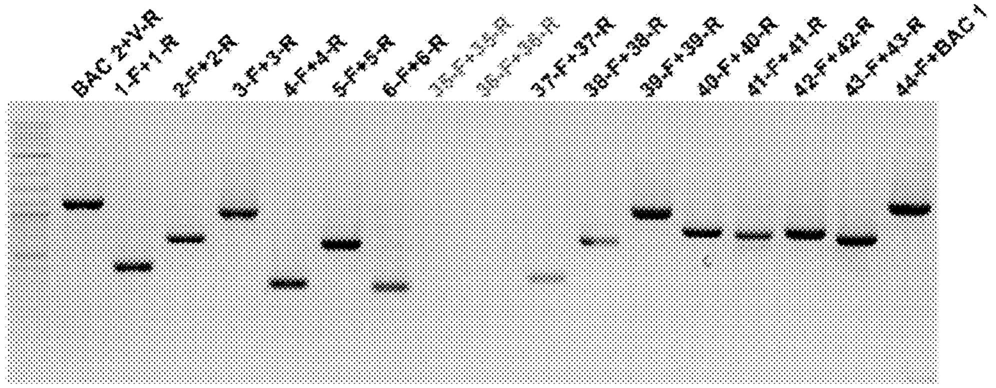
FIG. 5 is a schematic diagram of Junction PCR results of the intermediate plasmid 1 provided by an embodiment of the present invention.

3) Identification: a toothpick was used to pick the yeast transformants into sterilized $ddH_2O$, and even vortex mixing was carried out, with 4 cycles at 98° C., 3 min, 4° C., 2 min. Centrifugation was carried out at 6000 rpm for 5 min. By using supernatant as a template and using 6F/R and 41F/R as primers, PCR amplification was carried out, and the transformants were subjected to positive primary screening. A genome of yeast strains that were primarily screened as positive was extracted. Junction PCR verification was carried out by using a total of 18 pairs of primers, i.e., BAC2/V-R, 1F/1R to 6F/6R, 7F/7-35 JR, 35F/35R to 43F/43R and 44F/BAC1. Verification results are shown in FIG. 5, indicating that the intermediate plasmid 1 is successfully assembled in BY4741 cells. A map of the intermediate plasmid 1 is shown in FIG. 2.

2. Assembly of Intermediate Plasmid 2

1) Segment preparation: synthetic segments seg7-seg21 were obtained through Not I digestion, and by using pRS415 (publicly available plasmid, see Sikorski and Hieter, 1989) (-Leu) as a template, a pRS415 vector segment with homologous segments with seg7 and seg22 was amplified.

2) Yeast transformation: vector segments and segments seg7-seg21 were co-transformed into a yeast BY4742 (commercial strain, purchased from ZOMANBIO, Article Number: ZK280), and screening was carried out by using a screening medium SC-LEU to obtain transformants.

Figure 6:
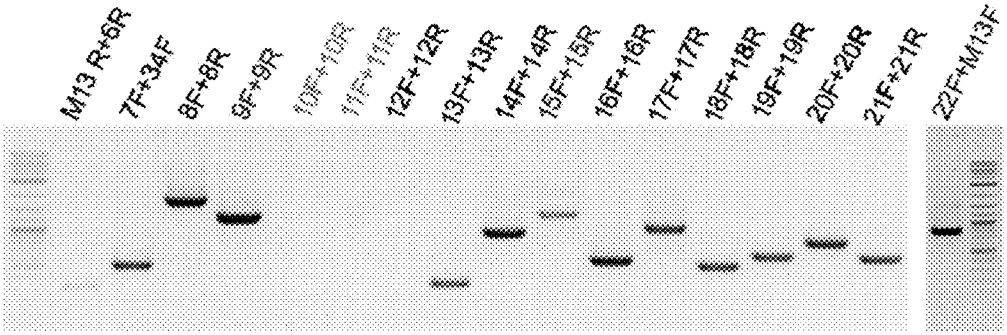
FIG. 6 is a schematic diagram of Junction PCR results of the intermediate plasmid 2 provided by an embodiment of the present invention.

3) Positive identification: a positive identification process was the same as that of an intermediate plasmid 2, and transformant positive primary screening primers were 7F/34F and 18F/R. Junction PCR verification was carried out by using a total of 14 pairs of primers, i.e., 7F/34F and 8F/8R to 20F/20R. Verification results are shown in FIG. 6, and the research results indicate that the intermediate plasmid 2 is successfully assembled in the yeast BY4742. A map of the intermediate plasmid 2 is shown in FIG. 3.

4) By using pFA6-kanMX4 (commercial plasmid, purchased from Shanghai Yaji Biotechnology Co., Ltd., Article Number: YC-14391RJ) as a template, through primers Met17F/R, PCR amplification was carried out to obtain a kanMX segment. The kanMXPCR segment was transformed into a yeast containing the intermediate plasmid 2, screening culture, and screening with SC-LEU+G418 were carried out; a transformed plate was photocopied onto a plate of G418, and monoclones that could grow on both plates were selected. Screening was carried out to obtain a yeast strain −2.

3. Assembly of Intermediate Plasmid 3

1) Segment preparation: synthetic segments seg22-seg35 were obtained through Not I digestion, and by using pRS411 (-Met) (publicly available plasmid, see Sikorski and Hieter, 1989) as a template, through primers pRS411VF+VR, PCR amplification was carried out to obtain a segment with homologous sequences with seg22 and seg35.

2) Yeast transformation: vector segments and segments seg22-seg35 were co-transformed into a yeast BY4741, and screening was carried out by using a screening medium SC-MET to obtain transformants.

Figure 7:
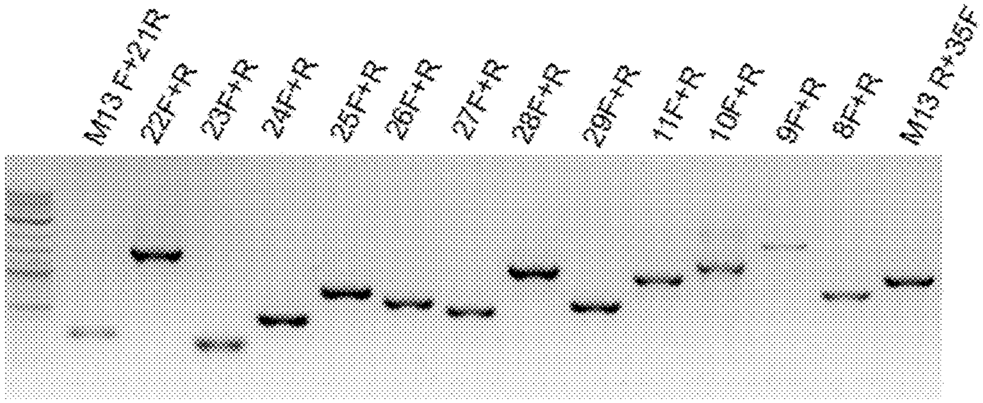
FIG. 7 is a schematic diagram of Junction PCR results of the intermediate plasmid 3 provided by an embodiment of the present invention.

3) Positive identification: a yeast transformant screening process was the same as that of an intermediate plasmid 3. Primary screening primers for transformant positive primary screening were 26F/R and 34F/R. Junction PCR verification was carried out on strains that were primarily screened positive by using a total of 13 pairs of primers, i.e., 22F/R to 29F/R, 8F/R to 11F/R and 34F/R. Verification results are shown in FIG. 7, and the research results indicate that the intermediate plasmid chunk3 is successfully assembled in the yeast BY4741. A map of the intermediate plasmid 3 is shown in FIG. 4.

4. Assembly of Complete Synthetic Chloroplast Genome

1) Obtaining Yeast Strain Haploid Containing Both Intermediate Plasmid 2 and Intermediate Plasmid 3

Figure 8:
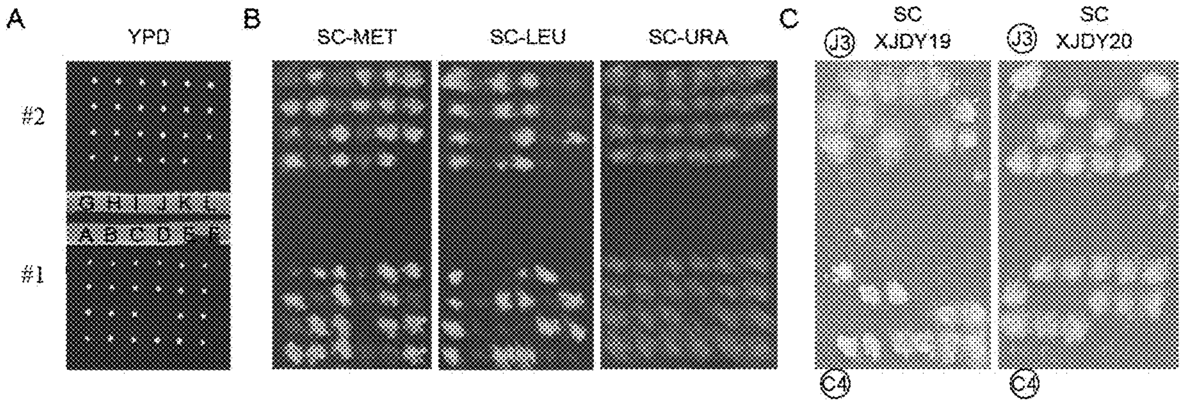
FIG. 8 is a schematic diagram of hybridization processes of yeasts containing the intermediate plasmid 1, the intermediate plasmid 2 and the intermediate plasmid 3 provided by an embodiment of the present invention.

Diploid yeast strains containing both the intermediate plasmid 2 (LEU2) and the intermediate plasmid 3 (MET17) were screened by using an SC-LEU-MET plate. The diploid yeast strains (#1, #2) were randomly selected from the SC-LEU-MET plate for spore production and spore division to obtain a haploid yeast (as shown in FIG. 8 A). A YPD plate was photocopied onto SC-LEU, SC-MET, and SC-URA plates, respectively. The SC-LEU and SC-MET plates were used for screening haploid yeast strains containing both the intermediate plasmid 2 and the intermediate plasmid 3. The SC-URA plate was used for ensuring that an obtained haploid did not grow on the SC-URA plate for subsequent hybridization of three intermediate plasmids. The haploid yeast strains containing both the intermediate plasmid 2 and the intermediate plasmid 3 were obtained (as shown in FIG. 8 B).

2) Obtaining Yeast Strain Containing all Intermediate Plasmid 1, Intermediate Plasmid 2 and Intermediate Plasmid 3

In order to subsequently hybridize with intermediate plasmid 1, it was necessary to select haploid yeast strains with a mating type of alpha from the haploid yeast strains. Mating types of SZU-JDYT9 (MAT a thr4 Mal') (Preservation Number: CCTCC M 20221034) and SZU-JDY20 (MAT alpha thr4 Mal') (Preservation Number: CCTCC M 20221033) were a and alpha, respectively, and a haploid strain that was hybridized with them could grow on an SD plate only after successfully hybridized into a diploid. The YPD spore division plates mentioned above were hybridized with SZU-JDY19 and SZU-JDY20, and then photocopied onto an SD plate to successfully screen a target strain, which was then, hybridized with a yeast strain containing the intermediate plasmid 1, and screening was carried out through an SC-LEU-MET-URA plate to obtain a yeast strain containing all three intermediate plasmids (as shown in FIG. 8 C).

Figure 9:
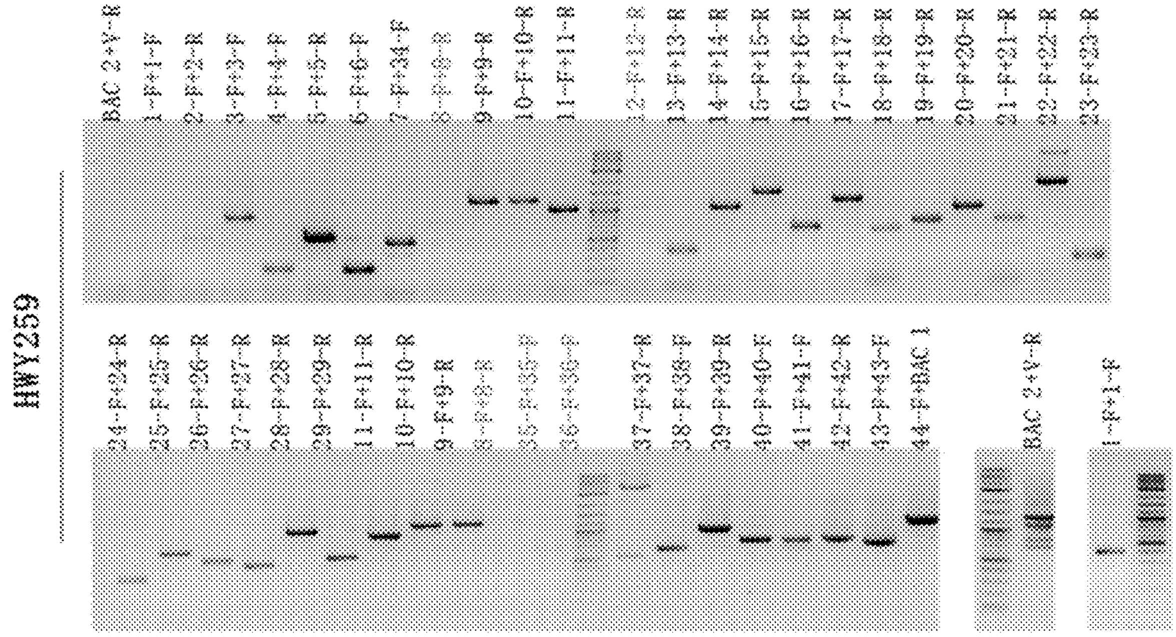
FIG. 9 is a schematic diagram of total Junction PCR verification results of the artificial chloroplast genome of *Chlamydomonas reinhardtii* provided by an embodiment of the present invention.

3) Assembly of Complete *Chlamydomonas reinhardtii* Chloroplast Genome by Three Intermediate Plasmids in Yeast Strain Among the three intermediate plasmids, each pair has a homologous segment. The intermediate plasmid 1 and the intermediate plasmid 2 both have segment 7, the intermediate plasmid 2 and the intermediate plasmid 3 both have segment 22, the intermediate plasmid 3 and the intermediate plasmid 1 both have segment 35, and one end of the homologous segment has an I-SceI cleavage site. I-SceI is an intron-encoded endonuclease of *Saccharomyces cerevisiae* mitochondria, which can specifically recognize about 18 bp sequences, and generate a double strand break nick at a recognition site to activate a homologous recombination repair mechanism of yeast cells. Transformation of an SZU-ZLP012 plasmid (Preservation Number: CCTCC M 20221031) was carried out. Screening was carried out by an SC-URA-LEU-MET-HIS plate. Expression of an I-SceI gene in a ZLP012 plasmid was induced by using a galactose to linearize the intermediate plasmid 1, the intermediate plasmid 2 and the intermediate plasmid 3. By means of the homologous recombination repair mechanism of yeast cells, assembly of a complete chloroplast genome with a BAC vector of the intermediate plasmid 1 as a vector was achieved. A genome of yeast strains was extracted. PCR screening was carried out by using 44 Junction primers to obtain a strain (Preservation Number: CCTCC M 20221035) containing a complete synthetic artificial chloroplast genome of *Chlamydomonas reinhardtii* (as shown in FIG. 9).

Embodiment 4 Function Verification of Artificial Chloroplast Genome of *Chlamydomonas reinhardtii*

1. Transfer of Chloroplast Artificial Genome into *Chlamydomonas reinhardtii* Chloroplast 1) Preparation of Gold Powder 30 mg of gold powder with a diameter of 1 μm was weighed and placed in a 1.5 mL centrifuge tube, 1 mL of 70% ethanol was added, Vigorous shake washing was carried out for 5 min, Soaking was carried out for 15 min. Centrifugation was carried out at 4000 rpm for 5 s, and the supernatant was discarded. 1 mL of $ddH_2O$ was added, Vigorous shake vortex was carried out for 1 min. Standing was carried out for 1 min. Repeated washing was carried out 3 times, and centrifugation was carried out at 4000 rpm for 5 min. 500 μL of 50% glycerol was added to a gold powder precipitate, and the gold powder precipitate was stored at 4° C. for standby use.

2) Envelope of Gold Powder

The gold powder stored in the 50% glycerol was fully shaken for 5 min, and 50 μL of the gold powder was taken and placed into a 1.5 mL centrifuge tube. 5 μg of a plasmid, 50 μL of $CaCl_2$) and 20 μL of 0.1 M spermidine were added at a time. Full vortex shaking was carried out for 3 min. Standing was carried out for 1 min. Centrifugation was carried out at 4000 rpm for 5 s. The supernatant was discarded, sufficient 70% ethanol was added for rinsing, and the supernatant was discarded, repeated twice. After rinsing, sufficient anhydrous ethanol was added for rinsing, and the supernatant was discarded. An appropriate amount of anhydrous ethanol was added. Quick vortex was carried out for 5 s. A precipitate was resuspended.

3) Biolistic Transformation

A receptor algal cell cultured to a cell concentration of $2\times10^6$ cell/mL was centrifuged (3500×g, 5 min) for collection, and resuspended with a fresh TAP medium to $1\times10^8$ cell/mL. 250 μL of a resuspended algal cell was taken, laid at a center of a 90×15 mm screening plate, and dried for 2 hours in dark at a room temperature. Preparation for bombardment DNA particles: 50 μL of gold powder was taken, add 5.0 μL of DNA (1.0 μg/μL), 50 μL of 2.5 M $CaCl_2$, and 20 μL of 0.1 mM spermidine were added in sequence, shaking for mixing well was carried out, centrifugation was carried out, washing was carried out with 70% alcohol, and finally resuspending was carried out with 100 μL of anhydrous ethanol, taking 10 μL for bombardment each time. A gene gun was Biolistic PDS-1000/He Particle Delivery System (BIO-RAD), with the following bombardment parameters: a crackable film 1100 psi, and a bombardment distance of 9 cm. After bombardment was completed, the plates were cultured in dark at 25° C. for 24 hours, and then transferred into an incubator at 25° C. with a photoperiodic ratio of 16:8 and continued to culture for 3-4 weeks until green monoclones grew.

2. Identification of Transformants

Figure 10:
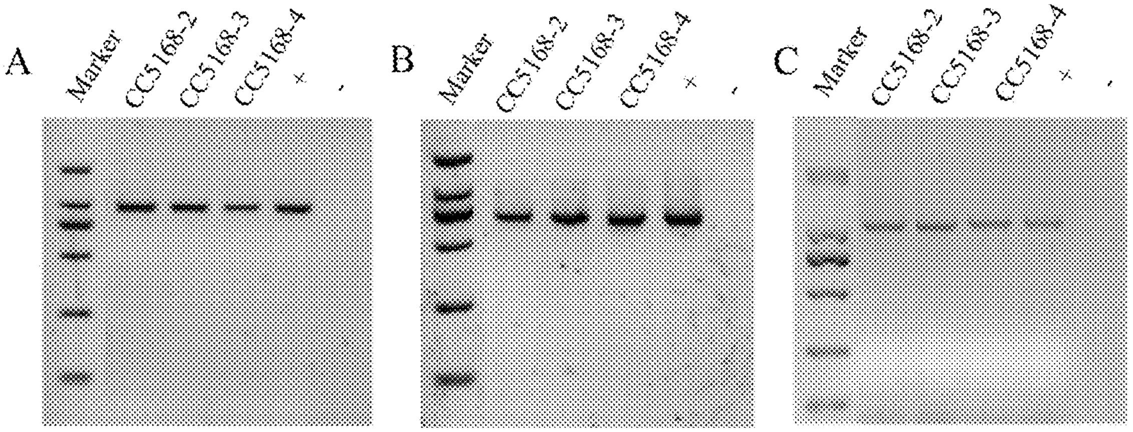
FIG. 10 is a schematic diagram of positive screening results of transformants of the artificial chloroplast genome of *Chlamydomonas reinhardtii* provided by an embodiment of the present invention.

After green transformants grew, in a super clean bench, the transformants were streaked with a toothpick to a new streptomycin resistance (150 μg/mL) culture dish, and continued to culture. *Chlamydomonas reinhardtii* monoclone cells were picked up to 50 μL of chelex. After shaking and mixing well at 98° C. for 30 min, immediate cooling was carried out on ice. Shaking for mixing well and centrifugation were carried out. By using a supernatant as a template and using 3×HA-1F/R and 3×HA-2 as primers for PCR amplification, transformant positive primary screening was carried out. Subsequently, a genome of transformants subjected to HA primary screening positive was extracted by using a genome extraction kit. By using the genome as a template, PCR amplification was carried out by using primers such as aphVIII-F/R, BAC44-F/R and BAC1-F/R. PCR products were subjected to 1.2% agarose gel electrophoresis for further positive identification to obtain transformants containing all HA tag, aphVIII and BAC sequences. Results are shown in FIG. 10, where A, aphVIII PCR identification; B, BAC-Seg1 PCR identification; C, BAC-seg44 PCR identification, in abc, Lane – has no template as negative control, Lane + is plasmid as positive control, Lanes CC125-K3, CC125-K6, CC125-M8, CC125-K2, CC125-N15, CC5168-2, CC5168-3 and CC5168-4 are transformants, and Marker is DL2000 bp.

3. Southern Blot Verification aphVIII and psaA specific amplification primers aphVIII-F1/R1 and psaA-F/R were designed, by using chunk2 as a template, PCR amplification was carried out to obtain aph VIII and psaA probe segments, and aphVIII and psaA probes were marked respectively by using DIG DNA Labeling and Detection Kit. Wild-type algal strain CC5168 (commercial strain purchased from *Chlamydomonas* Resource Center, USA) and transformant CC5168-3 were cultured to a logarithmic phase and centrifuged to collect algal cells. Hind III and EcoR V were selected to respectively subject 10-20 μg genome DNA to digestion at 37° C. for 6 h, and electrophoresis was carried out for 90 min at 80 V. In a 10×SSC transfer buffer solution, the genome DNA was transferred overnight to a positively charged nylon membrane, and then subjected to ultraviolet crosslinking (1500 V, 1.5 min) for fixation. The fixed nylon membrane was pre-hybridized for 30 min at 28° C. with 28° C. preheated DIG Easy Hyb Buffer. The pre-hybridized solution was discarded. Fresh 28° C. preheated DIG Easy Hyb Buffer (3.5 mL/100 $cm^2$) was added, and hybridization verification was carried out at 28° C. with aphVIII and psaA probes, refer to the instructions for specific operations.

Figure 11:
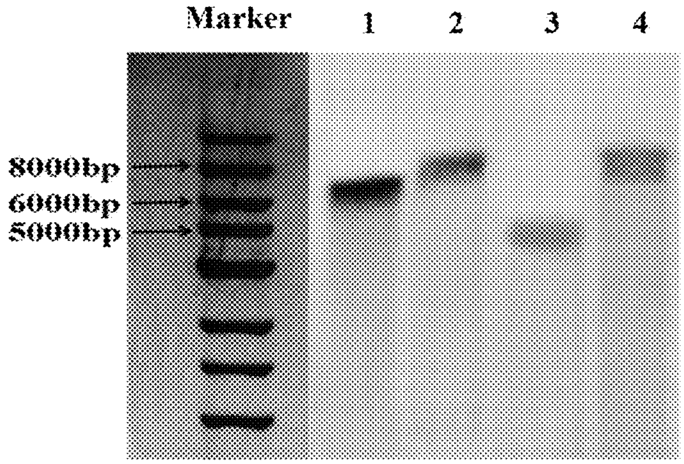
FIG. 11 is a schematic diagram of Southern Blot experiment results provided by an embodiment of the present invention.

Genome DNA of a photo-deficient algal strain CC5168 and a positive transformed algal strain CC5168-3 was subjected to enzymolysis with EcoR I and then respectively hybridized with the psaA probe. Results are shown in FIG. 11, where Lane 1 represents a hybridization result of enzymatic digestion of a wild-type CC125 genome by the psaA probe and the EcoR I; Lane 2 represents a hybridization result of enzymatic digestion of a CC125-N15 genome by the psaA probe and the EcoR I; Lane 3 represents a hybridization result of enzymatic digestion of the CC125-N15 genome by the aphVIII probe and Hind III; Lane 4 represents a hybridization result of enzymatic digestion of the CC125-N15 genome by the aphVIII probe and the EcoR I. Lane 1 is compared to Lane 2, and Lane 3 is compared to Lane 4. Marker is DL10000 bp. Results show that a hybrid band of *Chlamydomonas reinhardtii* CC5168 is approximately 6,681 bp, and a hybrid band of CC5168-3 is approximately 9000 bp, indicating that an aphVIII expression cassette exists in an artificially synthesized chloroplast genome. Subsequently, a genome of a positive transformed algal strain CC5168-3 was subjected to enzymolysis with EcoR I and Hind III, and subjected to Southern Blot with an aphVIII probe. Hybridization results show that a hybrid band of CC5168-3 genome DNA subjected to enzymolysis with the aphVIII probe and the EcoR I is approximately 9,000 bp, which is consistent with that with the psaA probe. Meanwhile, a hybrid band of CC5168-3 genome DNA subjected to enzymolysis with an aphVIII probe and Hind III is approximately 5,000 bp, indicating that an aphVIII expression cassette exists between 79,599 bp and 88,566 bp of an artificially synthesized chloroplast genome (FIG. 11), which is consistent with a location of an aphVIII expression cassette added in the artificially synthesized chloroplast genome during design. In RFLP-Southern Blot results of all transformants, only one band appears, indicating that transformed strains have been homogenized, and the artificially totally synthesized chloroplast genome has completely replaced the wild-type chloroplast genome.

4. Homogenization of Transformants

Figure 12:
FIG. 12 is a schematic diagram of culture results of transformants on TAP mediums with different streptomycin concentrations provided by an embodiment of the present invention.

Transformants identified by PCR were transferred onto resistant plates with streptomycin concentrations of 150 μg/mL, 300 μg/mL, 400 μg/mL, 500 μg/mL, 600 μg/mL, 700 μg/mL, 800 μg/mL, 900 μg/mL and 1000 μg/mL, and continued to be cultured in an incubator with a photoperiodic ratio of 16:8 (as shown in FIG. 12). Results show that when the streptomycin concentration is 300-900 μg/mL, the algal cells can grow normally, while the morphology of the algal cells with 1000 μg/mL changes significantly. 300, 600, and 900 μg/mL algal cell samples were taken and sent to a commercial company for sequencing.

5. Western Blot Verification

A photo-deficient algal strain CC5168 and transformants CC5168-3 and CC5168-6 were cultured to a logarithmic phase, and a total protein of algal cells was extracted. Finally, protein samples were suspended in a protein sample buffer solution (60 mM Tris pH 6.8, 2% (w/v) lauryl sodium sulfate, 10% (v/v) glycerol, 0.01% (w/v) bromophenol blue). The protein was separated with triglycine SDS-PAGE. Gel before immunoassay was subjected to Western Blot on a nitrocellulose membrane, by using HRP linked mouse antistreptococcic monoclonal antibody (1:5000, including 5% (w/v) BSA and milk powder (blocking agent) in TBS) or rabbit anti-glucose. Subsequently, the buffer solution was blocked by the antibody (1:5000 in a closed buffer solution) through HRP linked goat anti-Rabbit IgG (1:10000). A Pierce ECL Western Blot substrate and a Fusion Fx7 CCD camera were used for observation.

Figure 13:
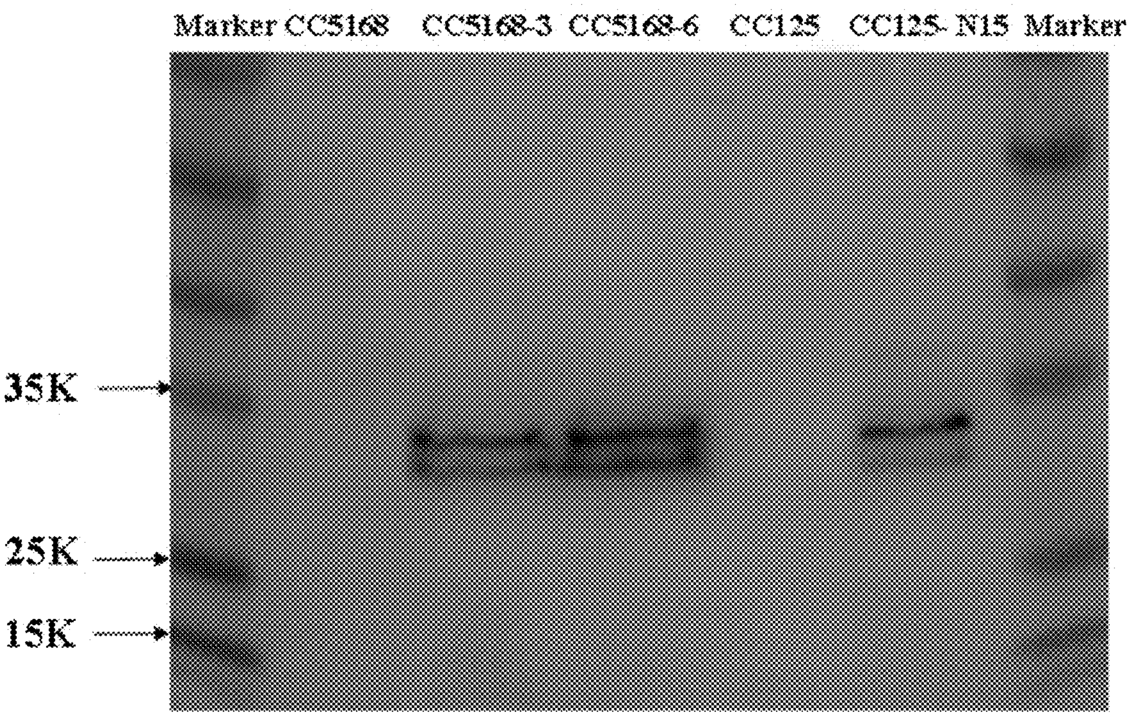
FIG. 13 is a schematic diagram of Western Blot experiment results provided by an embodiment of the present invention.

In order to study the protein expression in the artificial chloroplast genome of *Chlamydomonas reinhardtii*, HA tags were added to RPS4 (33.3 Kd) and ATPI (29.4 Kd) proteins. A total protein of *Chlamydomonas reinhardtii* CC5168 and transformants CC5168-3 and CC5168-6 thereof was extracted, and subjected to protein hybridization blot analysis with an HA monoclonal antibody. Results are shown in FIG. 13, where photo-deficient CC5168 and wild-type CC125 serve as a control group, CC5168-3 and CC5168-6 are positive transformed algal strains of CC5168, and CC125-N15 is a positive transformed algal strain of a CC125 synthetic genome. Experimental results show that the *Chlamydomonas reinhardtii* CC5168 has no hybridization blot, and the transformants CC5168-3 and CC5168-6 can be hybridized to an RPS4 protein with a size of 33.3 Kd and an ATPI protein with a size of 29.4 Kd (FIG. 13), indicating that marker proteins on the totally chemically synthesized artificial chloroplast genome of *Chlamydomonas reinhardtii* can be expressed normally, and the totally chemically synthesized genome has transcriptional and translational function activity.

6. Analysis of Photosynthetic Ability of Repair Photo Mutant Strain

1) Growth Curve

Figure 14:
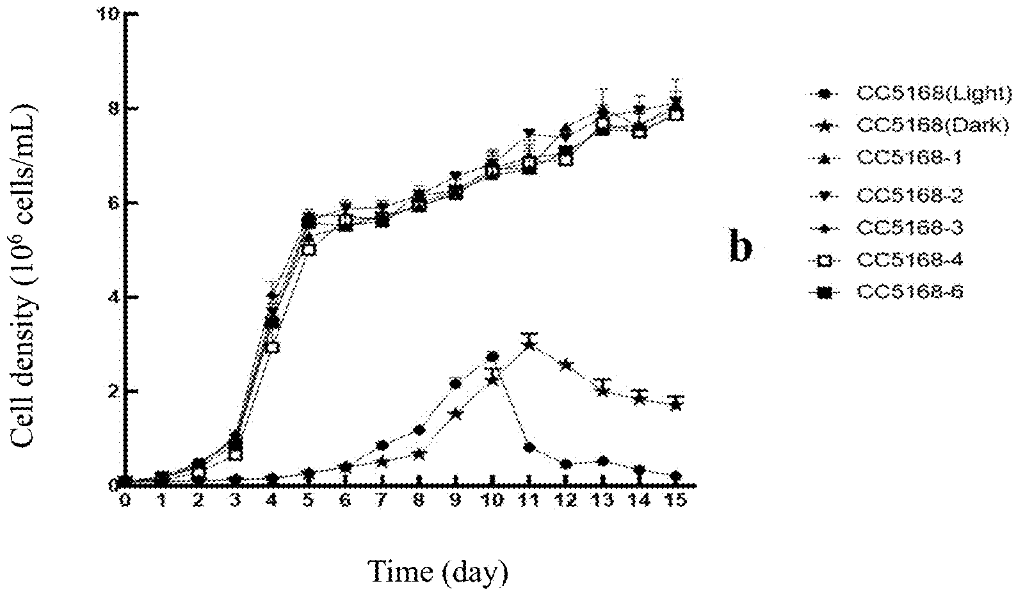
FIG. 14 is a schematic diagram of growth status results of CC5168 synthetic chloroplast algae strains provided by an embodiment of the present invention.

CC5168 and positive transformed algal strains CC5168-1, CC5168-2, CC5168-3, CC5168-4 and CC5168-6 were inoculated to a TAP liquid medium, under conditions of 25° C., 30 $\mu E/m^2/s$, light for 16 h, and dark for 8 h. In addition, CC5168 was inoculated to total dark as a control and cultured for 0 d, 1 d, 2 d, 3 d, 4 d, 5 d, 6 d, 7 d, 8 d, 9 d, 10 d, 11 d, 12 d, 13 d, 14 d and 15 d, respectively. OD750 values at different culture time were measured, and growth curves were plotted, as shown in FIG. 14. The growth status of the transformants was consistent with that of the receptor strains, indicating that the artificial chloroplast genome of *Chlamydomonas reinhardtii* could maintain the normal growth of algae cells. *Chlamydomonas reinhardtii* CC5168 was a psbH gene-deleted mutant strain that could not undergo photosynthesis and could only grow slowly under a condition of total dark, and had the number of cells reached $3\times10^4$ cells/mL after 11 days of cultivation, however, its transformant could grow under continuous light conditions of 22° C. and 30 $\mu mol\ m^{-2}\ s^{-1}$, and restored the growth status of the wild type, indicating that after the synthesized artificial chloroplast genome of *Chlamydomonas reinhardtii* entered *Chlamydomonas reinhardtii* CC5168 cells, the deletion mutation of psbH was repaired and the photoautotrophic function of the receptor strains was restored (FIG. 14).

2) Photosynthetic Efficiency

Algae cells cultured to a logarithmic phase were inoculated into a fresh TAP medium with an initial cell concentration of $4\times10^4$ cells/mL, and sampled daily after inoculation, and concentrations of cultured algae were calculated by using a cell counter until it grew to a plateau. Growth curves of different algae strains were plotted by using cell concentration obtained by counting as ordinate, and using growth time as abscissa. A Chlorophyll fluorometer PhytoPAM was used to measure Fv/Fm, Fv/Fo, and ΔF/Fm' of algae strains, refer to the PhytoPAM instructions for use for specific measurement methods. Results are shown in FIG. 15.

Figure 15:
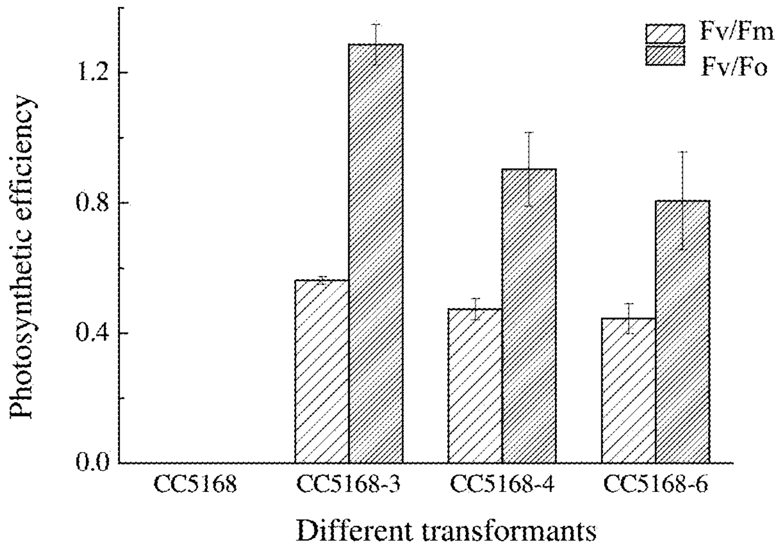
FIG. 15 is a schematic diagram of photosynthetic efficiency results of CC5168 transformants provided by an embodiment of the present invention.
Figure 16:
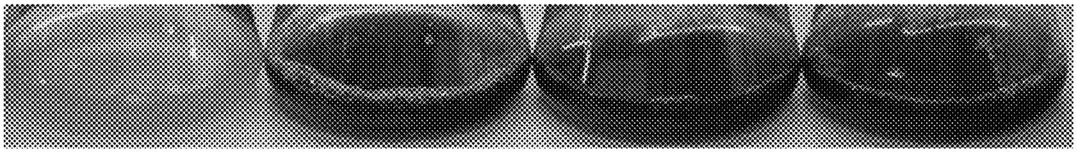
FIG. 16 is a schematic diagram of results of CC5168 synthetic chloroplast algae strains restoring normal growth under light provided by an embodiment of the present invention.

Research results show that under the continuous light conditions of 22° C. and 30 $\mu mol\ m^{-2}\ s^{-1}$, the *Chlamydomonas reinhardtii* CC5168 cannot undergo normal photosynthesis, and its transformants CC5168-2, 5168-3, 5168-4 and 5168-6 can undergo normal photosynthesis, indicating that the photosynthetic ability of *Chlamydomonas reinhardtii* CC5168 is restored (FIGS. 15 and 16).

In summary, the present invention provides a method for synthesis, assembly and function test of an artificial chloroplast genome of *Chlamydomonas reinhardtii*. According to the present invention, rational design has been carried out on the *Chlamydomonas reinhardtii* chloroplast genome for the first time, and total artificial synthesis of the *Chlamydomonas reinhardtii* chloroplast genome is proposed. By using the method of synthetic biology, all nucleic acid segments are constructed from chemically synthesized nucleic acid sequences. By using totally chemically synthesized chloroplast genome segments, total chemical de novo synthesis and assembly of a chloroplast genome are achieved in a yeast-bacterium system. Then, a totally chemically synthesized chloroplast genome is transformed into *Chlamydomonas* cells to replace the original chloroplast genome through various technical means, which works normally, and has been verified, fulfilling biological functions of the totally chemically synthesized chloroplast genome. The method can be widely applied in gene editing of the *Chlamydomonas reinhardtii* chloroplast genome and production of antibody drugs and the like, and has huge commercial advantages and broad market prospects. Meanwhile, according to the present invention, the *Chlamydomonas reinhardtii* chloroplast genome is an efficient platform for carrying out synthetic biology operation, the de novo design, total chemical synthesis, in vitro assembly and identification of the genome thereof provide a new solution for the rational design, modification and reconstruction of a photosynthetic system of photosynthetic organisms, improvement of photosynthetic efficiency of crops, and solving of agricultural crisis such as food security.

It should be understood that the application of the present invention is not limited to the above examples. For those of ordinary skill in the art, improvements or transformations can be made according to the above description, and all these improvements and transformations should fall within the protection scope of the claims attached to the present invention.

What is claimed is:

1. A method for synthesis, assembly, and function test of an artificial chloroplast genome of *Chlamydomonas reinhardtii*, the method comprising de novo design, total chemical synthesis, assembly and function verification of an artificial chloroplast genome of *Chlamydomonas reinhardtii*, wherein a nucleotide sequence of the artificial chloroplast genome of *Chlamydomonas reinhardtii* is obtained by designing and modifying a nucleotide sequence of a wild-type *Chlamydomonas reinhardtii* chloroplast genome and adding a BAC vector backbone, a streptomycin resistance gene aadA, a paromomycin resistance gene aphVIII and an HA tag, and wherein the nucleotide sequence of the artificial chloroplast genome of *Chlamydomonas reinhardtii* has a full length of 221,372 bp.

2. The method of claim 1, wherein the BAC vector backbone has a length of 11,060 bp, and an insertion site is located between 205,535 bp and 1 bp of the wild-type *Chlamydomonas reinhardtii* chloroplast genome; the streptomycin resistance gene aadA has a length of 1,630 bp, and an insertion site is located between 173,174 bp and 173,175 bp of the wild-type *Chlamydomonas reinhardtii* chloroplast genome; the paromomycin resistance gene aphVIII has a length of 2,287 bp, and an insertion site is located between 71,064 bp and 71,065 bp of the wild-type *Chlamydomonas reinhardtii* chloroplast genome; a 3×HA-1 tag is located behind atpI, and an insertion site is located between 170,786 bp and 170,787 bp of the wild-type *Chlamydomonas reinhardtii* chloroplast genome; a 3×HA-2 tag is located behind rps4, and an insertion site is located between 33,292 bp and 33,293 bp of the wild-type *Chlamydomonas reinhardtii* chloroplast genome.

3. The method of claim 1, wherein the function test of the artificial chloroplast genome of *Chlamydomonas reinhardtii* comprises the following steps:

transferring the artificial chloroplast genome of *Chlamydomonas reinhardtii* into a chloroplast of *Chlamydomonas reinhardtii* CC5168 by particle bombardment, and obtaining positive transformants by streptomycin screening, PCR and Southern Blot screening;

carrying out homogenization screening on the positive transformants by using gradient streptomycin resistance concentration; and carrying out Western Blot experiment on the positive transformants for verification of protein expression; and detecting a growth curve of the positive transformants and photosynthesis of a repair mutant strain.

4. The method of claim 3, wherein a probe used for Southern Blot verification of the positive transformants is obtained by amplification of aph VIII-F1/R1 and psaA-F/R primers, nucleotide sequences of the aph VIII-F1/R1 primer being shown in SEQ ID NO.1 and SEQ ID NO.2, and nucleotide sequences of the psaA-F/R primer being shown in SEQ ID NO.3 and SEQ ID NO.4.

* * * * *